US011761020B2

(12) United States Patent
Chang et al.

(10) Patent No.: US 11,761,020 B2
(45) Date of Patent: Sep. 19, 2023

(54) RECOMBINANT ADENO-ASSOCIATED VIRUS VECTORS WITH CD14 PROMOTER AND USE THEREOF

(71) Applicant: Aavocyte, Inc., Bellevue, WA (US)

(72) Inventors: Aiquan Chang, Bellevue, WA (US); Chuanxin Liu, Bellevue, WA (US); Yong Liu, Bellevue, WA (US)

(73) Assignee: Aavocyte, Inc., Bellevue, WA (US)

( * ) Notice: Subject to any disclaimer, the term of this patent is extended or adjusted under 35 U.S.C. 154(b) by 0 days.

(21) Appl. No.: 17/501,973

(22) Filed: Oct. 14, 2021

(65) Prior Publication Data

US 2022/0119842 A1 Apr. 21, 2022

Related U.S. Application Data

(60) Provisional application No. 63/092,239, filed on Oct. 15, 2020.

(51) Int. Cl.

| | | |
|---|---|---|
| C12N 15/861 | (2006.01) | |
| C12N 5/10 | (2006.01) | |
| C12N 5/0786 | (2010.01) | |
| C12N 5/0784 | (2010.01) | |
| C12N 15/11 | (2006.01) | |
| A61K 35/14 | (2015.01) | |
| A61K 39/00 | (2006.01) | |
| C12N 15/113 | (2010.01) | |
| C12N 15/86 | (2006.01) | |
| A61K 35/17 | (2015.01) | |
| C12N 5/0783 | (2010.01) | |
| C12N 15/864 | (2006.01) | |

(52) U.S. Cl.
CPC .............. *C12N 15/86* (2013.01); *A61K 35/17* (2013.01); *C12N 5/0638* (2013.01); *C12N 5/0639* (2013.01); *C12N 15/8645* (2013.01); *C12N 2501/22* (2013.01); *C12N 2501/2302* (2013.01); *C12N 2501/2304* (2013.01); *C12N 2501/2307* (2013.01); *C12N 2501/25* (2013.01); *C12N 2750/14134* (2013.01); *C12N 2750/14143* (2013.01); *C12N 2800/107* (2013.01); *C12N 2830/00* (2013.01); *C12N 2830/15* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 6,210,662 B1 | 4/2001 | Laus et al. | |
| 2010/0189742 A1* | 7/2010 | Van Der Burg | A61P 31/20 |
| | | | 435/372.3 |
| 2014/0329233 A1* | 11/2014 | Minshull | C12N 15/66 |
| | | | 435/6.1 |
| 2016/0120944 A1* | 5/2016 | Baylink | A61K 38/1858 |
| | | | 435/325 |
| 2018/0030553 A1* | 2/2018 | Tang | C12N 9/0008 |
| 2018/0369404 A1* | 12/2018 | Larson | C12N 15/62 |
| 2021/0079360 A1* | 3/2021 | Farley | C12N 9/22 |
| 2021/0290771 A1* | 9/2021 | Muzyczka | A61K 38/177 |

FOREIGN PATENT DOCUMENTS

| | | |
|---|---|---|
| CN | 101680002 A | 3/2010 |
| CN | 102268453 A | 12/2011 |
| CN | 102268454 A | 12/2011 |
| CN | 102268455 A | 12/2011 |
| CN | 102268456 A | 12/2011 |
| CN | 102268457 A | 12/2011 |
| CN | 102268458 A | 12/2011 |
| CN | 102277384 A | 12/2011 |
| CN | 105087647 B | 11/2015 |
| CN | 105087649 A | 11/2015 |
| CN | 105969804 A | 9/2016 |
| CN | 105985984 A | 10/2016 |
| CN | 105087648 B | 5/2018 |
| WO | 2018/200597 A1 | 11/2018 |
| WO | 2019/246261 A1 | 12/2019 |
| WO | WO 2016168264 * | 4/2020 |
| WO | 2020/191243 A1 | 9/2020 |

OTHER PUBLICATIONS

Yan et al, Inverted Terminal Repeat Sequences Are Important for Intermolecular Recombination and Circularization of Adeno-Associated Virus Genomes JVi, 2005, pp. 364-379.*
Singh et al, Overcoming the challenges associated with CD3+ T-cell redirection in cancer, BJC, 2020, pp. 1037-1048.*
Waldman et al, A guide to cancer immunotherapy: from T cell basic science to clinical practice, Nature, 2020, pp. 651-668.*
Kirtane et al, Adoptive cellular therapy in solid tumor malignancies: review of the literature and challenges ahead, Journal for ImmunoTherapy of Cancer 2021; pp. 1-11.*
Durgeau et al, Recent Advances in Targeting CD8 T-Cell Immunity for More Effective Cancer Immunotherapy, frontiers in Immunology, 2018, pp. 1-14.*
Holla et al, GM-CSF along with IL-4 but not alone is indispensable for the differentiation of human dendritic cells from monocytes, J Allergy Clin Immunol, 2014, pp. 1500-1502.*

(Continued)

*Primary Examiner* — Maria Marvich
(74) *Attorney, Agent, or Firm* — SEED INTELLECTUAL PROPERTY LAW GROUP LLP

(57) ABSTRACT

The present disclosure provides rAAV vectors and rAAV virions that specifically express exogenous nucleic acid sequences in CD14+ cells. The rAAV vectors or virions are useful for specifically expressing exogenous nucleic acid sequences encoding, for example, cancer antigens, viral antigens, and/or bacterial antigens in monocytes and dendritic cells. The rAAV transduced CD14+ cells can be used as antigen presenting cells that induce antigen-specific T cell responses. The present disclosure further provides methods producing rAAV virions and methods of immunotherapy.

30 Claims, 13 Drawing Sheets

Specification includes a Sequence Listing.

(56) References Cited

OTHER PUBLICATIONS

Valla et al, Cytokine-induced survival of activated T cells in vitro and in vivo, Proc. Natl. Acad. Sci. USA vol. 95, pp. 3810-3815, Mar. 1998.*

Chiriva-Internati, et al., "Testing recombinant adeno-associated virus-gene loading of dendritic cells for generating potent cytotoxic T lymphocytes against a prototype self-antigen, multiple myeloma HM1.24", *Blood,* Nov. 2003, vol. 102:9, pp. 3100-3107.

Liu, et al., "Rapid induction of cytotoxic T-cell response against cervical cancer cells by human papillomavirus type 16 E6 antigen gene delivery into human dendritic cells by an adeno-associated virus vector", *Cancer Gene Therapy,* vol. 8:12, 2001, pp. 948-957.

Liu, et al., "Use and specificity of breast cancer antigen/milk protein BA46 for generating anti-self-cytotoxic T lymphocytes by recombinant adeno-associated virus-based gene loading of dendritic cells", *Cancer Gene Therapy,* (2004), pp. 1-9.

Mahadevan, et al., "Generation of robust cytotoxic T lymphocytes against prostate specific antigen by transduction of dendritic cells using protein and recombinant adeno-associated virus", Cancer Immunol Immunother (2007) vol. 56, pp. 1615-1624.

Villadangos, et al., "Intrinsic and cooperative antigen-presenting functions of dendritic-cell subsets in vivo", *Nature Reviews | Immunology,* vol. 7, Jul. 2007, pp. 543-555.

Wang, et al., "A Preliminary Study of Adoptive T-cell Transfer Therapy for Patients With NonSmall-cell Lung Adenocarcinoma With Brain Metastasis: A Case Report of 3 Patients", *Clinical Lung Cancer,* vol. 21:4, Jul. 2020, pp. e270-e273.

Wang, et al., "Expression of Prostate-Specific Membrane Antigen in Lung Cancer Cells and Tumor Neovasculature Endothelial Cells and Its Clinical Significance", PLoS ONE 10(5): e0125924, May 15, 2015, pp. 1-8.

"*Homo sapiens* isolate ID 929 CD14 protein (CD14) gene, complete cds.," Database accession No. HQ199230, Feb. 2011, (2 pages).

Wang et al., "Efficient CFTR expression from AAV vectors packaged with promoters—the second generation," *Gene Therapy* 6:1999, (10 pages).

\* cited by examiner

FIG. 5

Homo sapiens isolate ID 929 CD14 protein (CD14) gene, complete cds
Sequence ID: HQ199230.1 Length: 5939 Number of Matches: 1

Range 1: 2986 to 3599 GenBankGraphics

| Score | Expect | Identities | Gaps | Strand |
|---|---|---|---|---|
| 1134 bits (614) | 0.0 | 614/614(100%) | 0/614(0%) | Plus/Plus |

```
Query  1     GTGCCAACAGATGAGGTTCACAATCTCTTCCACAAAACATGCAGTTAAATATCTGAGGAT  60
             ||||||||||||||||||||||||||||||||||||||||||||||||||||||||||||
Sbjct  2986  GTGCCAACAGATGAGGTTCACAATCTCTTCCACAAAACATGCAGTTAAATATCTGAGGAT  3045

Query  61    ATTCAGGGACTTGGATTTGGTGGCAGGAGATCAACATAAACCAAGACAAGGAAGAAGTCA  120
             ||||||||||||||||||||||||||||||||||||||||||||||||||||||||||||
Sbjct  3046  ATTCAGGGACTTGGATTTGGTGGCAGGAGATCAACATAAACCAAGACAAGGAAGAAGTCA  3105

Query  121   AAGAAATGAATCAAGTAGATTCTCTGGGATATAAGGTAGGGGGATTGGGGGGTTGGATAG  180
             |||||||||||||||||||||||||||||| |||||||||||||||||||||||||||||
Sbjct  3106  AAGAAATGAATCAAGTAGATTCTCTGGGATATAAGGTAGGGGCATTGGGGGGTTGGATAG  3165

Query  181   TGCAGAGTATGGTACTGGCCTAAGGCACTGAGGATCATCCTTTTCCCACACCCACCAGAG  240
             ||||||||||||||||||||||||||||||||||||:|||||||||||||||||||||||
Sbjct  3166  TGCAGAGTATGGTACTGGCCTAAGGCACTGAGGATCATCCTTTTCCCACACCCACCAGAG  3225

Query  241   AAGGCTTAGGCTCCCGAGTCAACAGGGCATTCACCGCCTGGGGCGCCTGAGTCATCAGGA  300
             ||||||||||||||||||||||||||||||||||||:|||||||||||||||||||||||
Sbjct  3226  AAGGCTTAGGCTCCCGAGTCAACAGGGCATTCACCGCCTGGGGCGCCTGAGTCATCAGGA  3285

Query  301   CACTGCCAGGAGACACAGAACCCTAGATGCCCTGCAGAATCCTTCCTGTTACGGCCCCCC  360
             ||||||||||||||||||||||||||||||||||||:|||||||||||||||||||||||
Sbjct  3286  CACTGCCAGGAGACACAGAACCCTAGATGCCCTGCAGAATCCTTCCTGTTACGGCCCCCC  3345

Query  361   TCCCTGAAACATCCTTCATTGCAATATTTCCAGGAAAGGAAGGGGGCTGGCTCGGAGGAA  420
             |||||||||||||||||||||||||||||||||'||||||||||||||||||||||||||
Sbjct  3346  TCCCTGAAACATCCTTCATTGCAATATTTCCAGGAAAGGAAGGGGGCTGGCTCGGAGGAA  3405

Query  421   GAGAGGTGGGGAGGTGATCAGGGTTCACAGAGGAGGGAACTGAATGACATCCCAGGATTA  480
             |||||||||||||||||||||||||||||||||:||||||||||||||||||||||||||
Sbjct  3406  GAGAGGTGGGGAGGTGATCAGGGTTCACAGAGGAGGGAACTGAATGACATCCCAGGATTA  3465

Query  481   CATAAACTGTCAGAGGCAGCCGAAGAGTTCACAAGTGTGAAGCCTGGAAGCCGGCGGGTG  540
             |||||||||||||||||||||||||||||||||:||||||||||||||||||||||||||
Sbjct  3466  CATAAACTGTCAGAGGCAGCCGAAGAGTTCACAAGTGTGAAGCCTGGAAGCCGGCGGGTG  3525

Query  541   CCGCTGTGTAGGAAAGAAGCTAAAGCACTTCCAGAGCCTGTCCGGAGCTCAGAGGTTCGG  600
             |||||||||||||||||||||||||||||||||||||'||||||||||||||||||||||
Sbjct  3526  CCGCTGTGTAGGAAAGAAGCTAAAGCACTTCCAGAGCCTGTCCGGAGCTCAGAGGTTCGG  3585

Query  601   AAGACTTATCGACC  614
             ||||||||||||||
Sbjct  3586  AAGACTTATCGACC  3599
```

Peripheral blood lymphocytes    Monocytes    Dendritic cells
The cells transfected with AAV/CD14 promoter/eGFP 293 cells transfected with AAV/CD14 promoter/eGFP

SEQUENCE LISTING

```
<160> NUMBER OF SEQ ID NOS: 6

<210> SEQ ID NO 1
<211> LENGTH: 614
<212> TYPE: DNA
<213> ORGANISM: Artificial Sequence
<220> FEATURE:
<223> OTHER INFORMATION: CD14 Promoter

<400> SEQUENCE: 1
gtgccaacag atgaggttca caatctcttc cacaaaacat gcagttaaat atctgaggat      60
attcagggac ttggatttgg tggcaggaga tcaacataaa ccaagacaag gaagaagtca     120
aagaaatgaa tcaagtagat tctctgggat ataaggtagg gggattgggg ggttggatag     180
tgcagagtat ggtactggcc taaggcactg aggatcatcc ttttcccaca cccaccagag     240
aaggcttagg ctcccgagtc aacagggcat tcaccgcctg gggcgcctga gtcatcagga     300
cactgccagg agacacagaa ccctagatgc cctgcagaat ccttcctgtt acggccccccc    360 tccctgaaac atccttcatt gcaatatttc caggaaagga aggggctgg ctcggaggaa      420 gagaggtggg gaggtgatca gggttcacag aggagggaac tgaatgacat cccaggatta     480
cataaactgt cagaggcagc cgaagagttc acaagtgtga agcctggaag ccggcgggtg     540
ccgctgtgta ggaaagaagc taaagcactt ccagagcctg tccggagctc agaggttcgg     600
aagacttatc gacc                                                       614

<210> SEQ ID NO 2
<211> LENGTH: 4151
<212> TYPE: DNA
<213> ORGANISM: Artificial sequence
<220> FEATURE:
<223> OTHER INFORMATION: Exemplary pAAV-CD14p vector DNA sequence

<400> SEQUENCE: 2
ggtaccgcta gcctgcaggg ggggggggcc cccttggcca ctccctctct gcgcgctcgc      60
tcgctcactg aggccgggcg accaaaggtc gcccgacgcc cgggctttgc ccgggcggcc     120
tcagtgagcg agcgagcgcg cagagaggga gtggccaact ccatcactag gggttcctgg     180 agggggtggag tcgtgacatc agatccatgc ggccgcaccg tattaccgcc atgcatgtgc     240
caacagatga ggttcacaat ctcttccaca aaacatgcag ttaaatatct gaggatattc     300
agggacttgg atttggtggc aggagatcaa cataaaccaa gacaaggaag aagtcaaaga     360
aatgaatcaa gtagattctc tgggatataa ggtaggggga ttgggggggtt ggatagtgca     420
```

```
gagtatggta ctggcctaag gcactgagga tcatccttt  cccacaccca ccagagaagg    480
cttaggctcc cgagtcaaca gggcattcac cgcctgggc  gcctgagtca tcaggacact    540
gccaggagac acagaaccct agatgccctg cagaatcctt cctgttacgg ccccctccc    600 tgaaacatcc ttcattgcaa tatttccagg aaaggaaggg gctggctcg gaggaagaga    660 ggtggggagg tgatcagggt tcacagagga gggaactgaa tgacatccca ggattacata    720
aactgtcaga ggcagccgaa gagttcacaa gtgtgaagcc tggaagccgg cgggtgccgc    780
tgtgtaggaa agaagctaaa gcacttccag agcctgtccg gagctcagag gttcggaaga    840
cttatcgacc agatctacga tctcgaggtc gagctgtcta gacgagcaga catgataaga    900
tacattgatg agtttggaca aaccacaact agaatgcagt gaaaaaaatg ctttatttgt    960
gaaatttgtg atgctattgc tttatttgta accattataa gctgcaataa acaagttaac   1020
aacaacaatt gcattcattt tatgtttcag gttcagggg  aggtgtggga ggtttttaa   1080 agcaagtaaa acctctacaa atgtggtact taaggatgta gataagtagc atggcgggtt   1140
aatcattaac tacaaggaac ccctagtgat ggagttggcc actccctctc tgcgcgctcg   1200
ctcgctcact gaggccgggc gaccaaaggt cgcccgacgc ccgggctttg cccgggcggc   1260
ctcagtgagc gagcgagcgc gcagagaggg agtggccaag gggggggggg ggggggggc   1320 cccctgcag  gaattcggat ccgtcgaccg atgcccttga gagccttcaa cccagtcagc   1380
tccttccggt gggcgggg  catgactatc gtcgccgcac ttatgactgt cttctttatc   1440
atgcaactcg taggacaggt gccggcagcg ctcttccgct tcctcgctca ctgactcgct   1500
gcgctcggtc gttcggctgc ggcgagcggt atcagctcac tcaaaggcgg taatacggtt   1560
atccacagaa tcaggggata acgcaggaaa gaacatgtga gcaaaaggcc agcaaaaggc   1620
caggaaccgt aaaaaggccg cgttgctggc gtttttccat aggctccgcc ccctgacga    1680 gcatcacaaa aatcgacgct caagtcagag gtggcgaaac ccgacaggac tataaagata   1740
ccaggcgttt ccccctggaa gctccctcgt gcgctctcct gttccgaccc tgccgcttac   1800
cggatacctg tccgcctttc tcccttcggg aagcgtggcg ctttctcata gctcacgctg   1860
taggtatctc agttcggtgt aggtcgttcg ctccaagctg ggctgtgtgc acgaaccccc   1920
cgttcagccc gaccgctgcg ccttatccgg taactatcgt cttgagtcca acccggtaag   1980
acacgactta tcgccactgg cagcagccac tggtaacagg attagcagag cgaggtatgt   2040
aggcggtgct acagagttct tgaagtggtg gcctaactac ggctacacta agaacagt    2100 atttggtatc tgcgctctgc tgaagccagt taccttcgga aaaagagttg gtagctcttg   2160
atccggcaaa caaaccaccg ctggtagcgg tggtttttt  gtttgcaagc agcagattac   2220
gcgcagaaaa aaggatctc  aagaagatcc tttgatcttt tctacggggt ctgacgctca   2280
gtggaacgaa aactcacgtt aagggatttt ggtcatgaga ttatcaaaaa ggatcttcac   2340
ctagatcctt ttaaattaaa aatgaagttt taaatcaatc taaagtatat atgagtaaac   2400
ttggtctgac agttaccaat gcttaatcag tgaggcacct atctcagcga tctgtctatt   2460
tcgttcatcc atagttgcct gactccccgt cgtgtagata actacgatac gggagggctt   2520
accatctggc cccagtgctg caatgatacc gcgagaccca cgctcaccgg ctccagattt   2580
atcagcaata accagccag  ccggaagggc cgagcgcaga agtggtcctg caactttatc   2640
cgcctccatc cagtctatta attgttgccg ggaagctaga gtaagtagtt cgccagttaa   2700
tagttttcgc aacgttgttg ccattgctac aggcatcgtg gtgtcacgct cgtcgtttgg   2760
tatggcttca ttcagctccg gttcccaacg atcaaggcga gttacatgat cccccatgtt   2820
```

```
gtgcaaaaaa gcggttagct ccttcggtcc tccgatcgtt gtcagaagta agttggccgc    2880
agtgttatca ctcatggtta tggcagcact gcataattct cttactgtca tgccatccgt    2940
aagatgcttt tctgtgactg gtgagtactc aaccaagtca ttctgagaat agtgtatgcg    3000
gcgaccgagt tgctcttgcc cggcgtcaat acgggataat accgcgccac atagcagaac    3060
tttaaaagtg ctcatcattg gaaaacgttc ttcggggcga aaactctcaa ggatcttacc    3120
gctgttgaga tccagttcga tgtaacccac tcgtgcaccc aactgatctt cagcatcttt    3180
tactttcacc agcgtttctg ggtgagcaaa acaggaagg caaaatgccg caaaaaggg    3240 aataagggcg acacggaaat gttgaatact catactcttc cttttcaat attattgaag    3300 catttatcag ggttattgtc tcatgagcgg atacatattt gaatgtattt agaaaaataa    3360
acaaataggg gttccgcgca catttccccg aaaagtgcca cctgacgcgc cctgtagcgg    3420
cgcattaagc gcggcgggtg tggtggttac gcgcagcgtg accgctacac ttgccagcgc    3480
cctagcgccc gctcctttcg ctttcttccc ttcctttctc gccacgttcg ccggctttcc    3540
ccgtcaagct ctaaatcggg ggctcccttt agggttccga tttagtgctt tacggcacct    3600
cgaccccaaa aaacttgatt agggtgatgg ttcacgtagt gggccatcgc cctgatagac    3660
ggtttttcgc cctttgacgt tggagtccac gttctttaat agtggactct tgttccaaac    3720
tggaacaaca ctcaacccta tctcggtcta ttcttttgat ttataaggga ttttgccgat    3780
ttcggcctat tggttaaaaa atgagctgat ttaacaaaaa tttaacgcga attttaacaa    3840
aatattaacg cttacaattt gccattcgcc attcaggctg cgcaactgtt gggaagggcg    3900
atcggtgcgg gcctcttcgc tattacgcca gcccaagcta ccatgataag taagtaatat    3960
taaggtacgg gaggtacttg gagcggccgc aataaaatat ctttattttc attacatctg    4020
tgtgttggtt ttttgtgtga atcgatagta ctaacatacg ctctccatca aaacaaaacg    4080
aaacaaaaca aactagcaaa ataggctgtc cccagtgcaa gtgcaggtgc cagaacattt    4140
ctctatcgat a                                                         4151

<210> SEQ ID NO 3
<211> LENGTH: 46
<212> TYPE: DNA
<213> ORGANISM: Artificial Sequence
<220> FEATURE:
<223> OTHER INFORMATION: Downstream primer with MCS linker (SnaB I, Bgl
      II, Xba I)

<400> SEQUENCE: 3
attacgtagc agatctagtc tctagaggtc gataagtctt ccgaac                   46

<210> SEQ ID NO 4
<211> LENGTH: 27
<212> TYPE: DNA
<213> ORGANISM: Artificial sequence
<220> FEATURE:
<223> OTHER INFORMATION: Upstream primer with BmgBI linker

<400> SEQUENCE: 4
atgacgtggt gccaacagat gaggttc                                        27

<210> SEQ ID NO 5
<211> LENGTH: 20
<212> TYPE: DNA
<213> ORGANISM: Artificial sequence
<220> FEATURE:
<223> OTHER INFORMATION: Downstream primer for human CD14 promoter
```

```
                           sequence

<400> SEQUENCE: 5
ggtcgataag tcttccgaac                                              20

<210> SEQ ID NO 6
<211> LENGTH: 19
<212> TYPE: DNA
<213> ORGANISM: Artificial sequence
<220> FEATURE:
<223> OTHER INFORMATION: Upstream primer for human CD14 promoter
                           sequence

<400> SEQUENCE: 6
gtgccaacag atgaggttc                                               19
```

RECOMBINANT ADENO-ASSOCIATED VIRUS VECTORS WITH CD14 PROMOTER AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 100239_401_SEQUENCE_LISTING.txt. The text file is 7.6 KB, was created on Sep. 15, 2021, and is being submitted electronically via EFS-Web.

BACKGROUND

Technical Field

The present invention relates to the field of molecular biology, immunology, immunotherapy, and gene therapy. Specifically, the present invention relates to a recombinant adeno-associated virus vector with a CD14 promoter region and its practical applications.

Description of the Related Art

Adeno-associated virus (AAV) type 2 genome is built of single-stranded deoxyribonucleic acid (ssDNA), which is about 4.7 kilobase long. The AAV genome comprises inverted terminal repeat (ITR) sequences (145 base) at both ends of AAV DNA strand, and two open reading frames (ORFs): rep and cap gene. On the left side of AAV genome there are p5, p19, and p40 promoters, from which two overlapping mRNA of different length can be produced.

Since AAV is a non-pathogenic virus, it is utilized as a viral vector for gene therapy and immunotherapy. AAV and recombinant adeno-associated virus (rAAV) have the ability to widely infect (transduce) various human cells, such as somatic cells, nerve cells, and hematocytes, and others. The rAAV can express exogenous RNA that may be translated into polypeptides. This infectious nature of rAAV has advantages in gene therapy for many diseases. However, rAAV vectors usually contain constitutive promoters, such as AAV promoters, CMV promoters, SV40 early promoters and others, which can facilitate expression of the gene in all or many tissues. The rAAV with a constitutive promoter can produce undesired off-target effects by infecting non-target cells and expressing the product of exogenous gene in the non-target cells. Therefore, in clinical treatment, a rAAV having a constitutive promoter may lead to adverse reactions or side effects unrelated to the purpose of treatment, including potential risks of toxic effects. Therefore, there is a need in the art for a rAAV vector with improved safety, accuracy, and efficacy of treatment.

BRIEF SUMMARY

The present disclosure provides a polynucleotide, comprising a recombinant adeno-associated virus (rAAV) vector encoding two inverted terminal repeat (ITR) sequences and a CD14 promoter operably linked to an exogenous nucleic acid sequence, wherein the CD14 promoter induces expression of the exogenous nucleic acid specifically in a CD14-expressing cell. In some embodiments, the CD14 promoter is a human CD14 promoter sequence. In some embodiments, the CD14 promoter comprises SEQ ID NO:1. In some embodiments, the CD14 promoter comprises at least the nucleotides at positions 378-386, positions 404-410, and positions 533-538 of SEQ ID NO:1. In some embodiments, the CD14-expressing cell is a monocyte, macrophage, or dendritic cell. In some embodiments, the rAAV vector comprises in the 5' to 3' direction a first ITR, the CD14 promoter operably linked to the exogenous nucleic acid sequence, a polyadenylation signal sequence, and a second ITR. In some embodiments, the exogenous nucleic acid sequence comprises a multiple cloning site (MCS), a restriction enzyme target sequence, and/or a sequence encoding a polypeptide. In some embodiments, the sequence encoding a polypeptide encodes all or part of a tumor antigen, tumor-associated antigen, oncogene product, viral antigen, a bacterial antigen, a cytokine, or any combination thereof.

In some embodiments, the present disclosure provides an rAAV virion, comprising the polynucleotide comprising two ITR sequences and a CD14 promoter operably linked to an exogenous nucleic acid sequence, wherein the CD14 promoter induces expression of the exogenous nucleic acid specifically in a CD14-expressing cell. In some embodiments, the rAAV virion comprises capsid proteins of AAV1, AAV2, AAV3, AAV4, AAV5, AAV6, AAV7, AAV8, AAV9, AAV10, AAV11, or any combination thereof.

In some embodiments, the present disclosure provides a method of producing an rAAV virion, comprising introducing an rAAV vector disclosed herein into a packaging cell, wherein the packaging cell comprises one or more nucleic acid sequences encoding helper genes. In some embodiments, the helper genes comprise AAV Rep and Cap genes and adenoviral VA, E2A, E3 and E4 genes. In some embodiments, the method of producing an rAAV virion comprises co-transfecting the helper genes into the packaging cell with the rAAV vector disclosed herein. In some embodiments, the packaging cell is a HEK 293, HeLa, or HT1080 cell.

In some embodiments, the present disclosure provides a population of isolated cells comprising any one of the rAAV vectors disclosed herein. In some embodiments, the cells express CD14. In some embodiments, the cells are monocytes, dendritic cells, or macrophages.

In some embodiments, the present disclosure provides a pharmaceutical composition comprising the isolated rAAV transduced CD14$^+$ cells disclosed herein, wherein the cells are effective to activate T cells to produce an antigen-specific immune response against the polypeptide encoded by the exogenous nucleic acid sequence. In some embodiments, the polypeptide is a tumor antigen, tumor-associated antigen, oncogene product, viral antigen, or bacterial antigen. In some embodiments, the cells are monocytes, dendritic cells, or macrophages.

In some embodiments, the present disclosure provides a pharmaceutical composition comprising antigen-specific T cells that target cells expressing the polypeptide encoded by the exogenous nucleic acid sequence disclosed herein, wherein the T cells have been activated by the cells of any one of rAAV transduced CD14$^+$ cells disclosed herein.

In some embodiments, the present disclosure provides a pharmaceutical composition comprising human peripheral blood mononuclear cells (PBMCs), wherein the PBMCs comprise antigen-specific T cells that have been activated by the rAAV transduced CD14$^+$ cells disclosed herein.

In some embodiments, the present disclosure provides a method of immunotherapy comprising administering the population of isolated cells disclosed herein or the pharmaceutical composition disclosed herein to a subject in need thereof, thereby stimulating an immune response. In some embodiments, the subject is a human.

In some embodiments, the present disclosure provides a method of immunotherapy, comprising: a. infecting PBMCs of a subject with an rAAV virion disclosed herein to generate infected PBMCs, b. adding a differentiating cytokine to differentiate monocytes of the infected PBMCs into dendritic cells (DCs), c. adding an activating cytokine to activate cytotoxic T lymphocytes (CTLs) of the infected PBMCs to generate activated CTLs, d. optionally isolating activated CTLs from the infected PBMCs, and e. administering an effective amount of the infected PMBCs that comprise activated CTLs or isolated activated CTLs to the subject.

In some embodiments, the present disclosure provides a method of producing a modified antigen presenting cell (APC), comprising: i) providing a CD14+ cell; ii) contacting the CD14+ cell with the rAAV virion disclosed herein, sufficient to express the sequence encoding a polypeptide; and iii) culturing the CD14+ cell of step ii) for a time sufficient to express the polypeptide. In some embodiments, the CD14+ cell is a monocyte or a dendritic cell. In some embodiments, the monocyte is in a population of PBMCs. In some embodiments, the monocyte is an isolated monocyte. In some embodiments, the monocyte is further differentiated into a dendritic cell. In some embodiments, the monocyte is differentiated into a dendritic cell by contacting the monocyte with an exogenous cytokine. In some embodiments, the exogenous cytokine is GM-CSF, IL-4, TNF-α, or any combination thereof.

In some embodiments, the present disclosure provides a method of producing an antigen-specific T cell, comprising: i) providing a naïve T cell; ii) contacting the naïve T cell with the modified APC produced disclosed herein; and iii) contacting the T cell of step ii) with an activating cytokine. In some embodiments, the activating cytokine is IL-2, IL-7, or both. In some embodiments, the antigen-specific T cell is a CD4+ T cell or a CD8+ T cell.

BRIEF DESCRIPTION OF THE DRAWINGS

Some embodiments of the present disclosure are illustrated as an example and are not limited by the accompanying drawings:

FIG. 5 shows an alignment of the sequence of human CD14 promoter DNA (SEQ ID NO:1) in the exemplary pAAV-CD14p plasmid compared to a reference wild-type sequence (GenBank Accession No. HQ199230.1).

DETAILED DESCRIPTION

Figure 1:
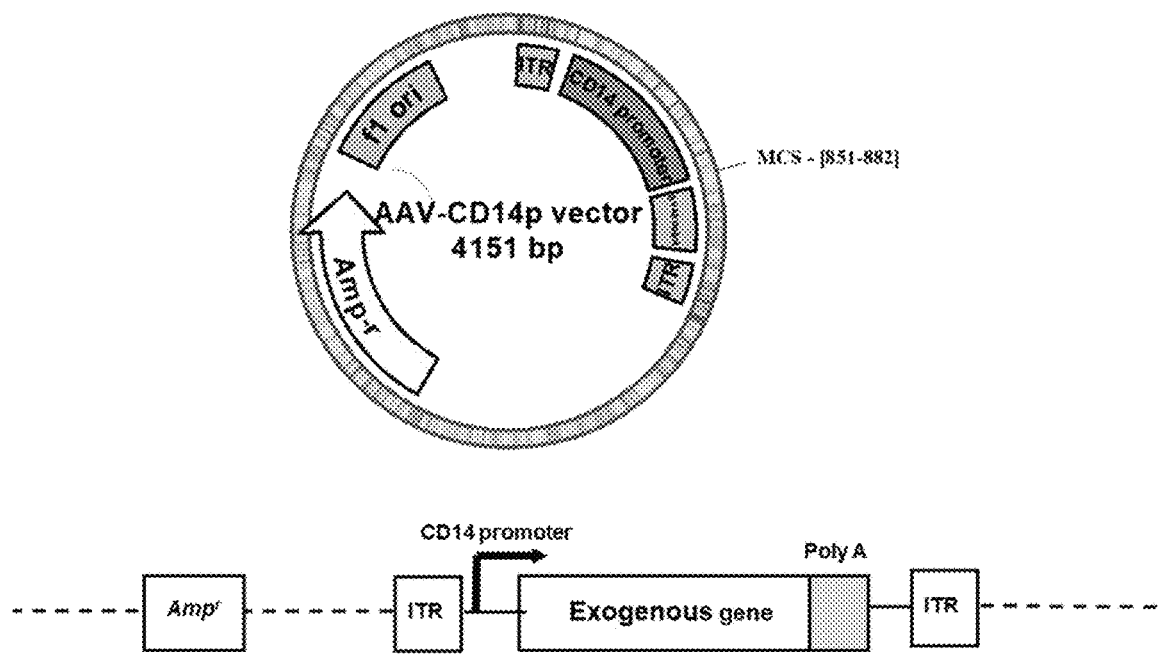
FIG. 1 illustrates the schematic diagram of an exemplary AAV/Human CD14 promoter vector (an exemplary pAAV-CD14p) for expressing an exogenous gene.

Provided herein are recombinant adeno-associated virus (rAAV) vectors that include a cluster of differentiation antigen 14 (CD14) promoter that can promote targeted and/or specific expression of an operably linked polynucleotide in CD14+ cells, such as monocytes or dendritic cells (DC). An exogenous gene and/or coding sequence can be inserted into the rAAV vector. Also provided are rAAV virions (e.g., rAAV-CD14p) capable of infecting CD14+ cells and introducing an exogenous gene and/or coding sequence that is operably linked to a CD14 promoter, thereby promoting targeted and/or specific expression of the exogenous gene and/or coding sequence in the CD14+ cells. Examples of exogenous genes and/or coding sequences include, but are not limited to, sequences encoding wild type, truncated or mutant tumor antigen genes, tumor-associated antigens, viral antigens, bacterial antigens, cytokines and other polypeptides of interest. The rAAV vectors and virions disclosed herein are useful in transducing monocytes and DC to induce immune responses that can be used to treat or prevent malignant tumors, viral or bacterial infectious diseases, and other diseases. Using a tissue- or cell-specific CD14 promoter, the rAAV vectors, compositions, methods disclosed herein provide the advantage of targeted and/or specific expression of the polynucleotide sequence of interest in CD14+ cells, while reducing complications that may result from expression in non-target cells.

Definitions

In the present description, any concentration range, percentage range, ratio range, or integer range is to be understood to include any values or subranges within the recited range unless otherwise indicated. As used herein, the term "about" means±20% of the indicated range or value unless otherwise indicated.

It should also be noted that the term "or" is generally employed in its sense including "and/or" (i.e., to mean either one, both, or any combination thereof of the alternatives) unless the content dictates otherwise.

Also, as used in this specification and the appended claims, the singular forms "a," "an," and "the" include plural referents unless the content dictates otherwise.

The terms "include," "have," "comprise" and their variants are used synonymously and to be construed as non-limiting.

The term "a combination thereof" as used herein refers to all possible combinations of the listed items preceding the term. For example, "A, B, C, or a combination thereof" is intended to refer to any one of: A, B, C, AB, AC, BC, or ABC. Similarly, the term "combinations thereof" as used herein refers to all possible combinations of the listed items preceding the term. For instance, "A, B, C, and combinations thereof" is intended to refer to all of: A, B, C, AB, AC, BC, and ABC.

As used herein, the terms "polynucleotide," "nucleotide," "nucleotide sequence," "nucleic acid" and "oligonucleotide" are used interchangeably and refer to a deoxyribonucleotide or ribonucleotide polymer, in linear or circular conformation, and in either single- or double-stranded form. Examples of polynucleotides include coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

As used herein, the terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

In general, and as used herein, the term "vector" refers to a polynucleotide capable of transporting another polynucleotide to which it has been linked. Vectors include, but are not limited to, polynucleotide molecules that are single-stranded double-stranded, or partially double-stranded; polynucleotide molecules that comprise one or more free ends, no free ends (e.g., circular); polynucleotide molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., adeno-associated viruses). Viral vectors also include polynucleotides carried by a virus for transduction into a host cell.

The term "transfection" and "transduction" are interchangeable and refer to the process by which an exogenous DNA sequence is introduced into a eukaryotic cell. Transfection can be achieved by any one of a number of methods including electroporation, microinjection, gene gun delivery, lipofection, superfection, etc. Transduction generally refers to introduction of an exogenous DNA sequence into a eukaryotic cell achieved by a viral vector, such as an AAV, retroviral, lentiviral, or adenoviral vector.

As used herein, a "gene" includes a DNA sequence encoding a polynucleotide or polypeptide. Accordingly, a gene may include, but is not necessarily limited to, cDNA sequences, genomic sequences, and smaller engineered gene segments that express, or are adapted to express, proteins, polypeptides, domains, peptides, fusion proteins, and/or mutants.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as an "expression product."

As used herein, "specific expression," "targeted expression," and "specifically express" are used interchangeably and refer to the expression of a polynucleotide or polypeptide in a particular target tissue or target cell-type, but lack of expression or undetectable expression in non-target tissues or non-target cell-types. Specific expression is usually driven by a "tissue-specific promoter" or "cell-specific promoter." A "tissue specific promoter" expresses a gene under its control in one or a few target tissues, but not other tissues. A "cell-specific promoter" expresses a gene under its control in one or a few specific cell types, but not other cell types. Both tissue-specific promoters and cell-specific promoters may be referred to as "specific promoters" as used herein. A specific promoter contains specific DNA sequences that interact with one or more particular transcription factors that can act as activators and/or repressors of transcription. A specific promoter drives expression of a polynucleotide only in certain cell-types and/or tissues. For example, a specific promoter can drive specific expression of a polynucleotide in a monocyte and/or DC, but not in a T cell or epithelial cell. An example of a specific promoter is a CD14 promoter.

As used herein, "operably linked" is intended to mean that the nucleotide sequence of interest is linked to the regulatory element(s), such as a promoter, in a manner that allows for expression of the nucleotide sequence in, e.g., a host cell when a vector is introduced into the host cell.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel (1990) Gene Expression Technology: Methods in Enzymology 185, Academic Press, San Diego, Calif. Regulatory elements include those that direct tissue specific expression.

The term "rAAV virion" or "rAAV particle" as used herein refers to an infectious virus particle comprising a capsid comprising at least one AAV capsid protein that encapsidates an rAAV vector as described herein. Preferably, the vector comprises an exogenous and/or heterologous nucleic acid sequence that is expressed after the rAAV virion infects (transduces) a target cell.

As used herein, "exogenous" refers to a nucleic acid sequence or polypeptide that is not normally present in a cell or virus, but can be introduced into a cell or virus by one or more genetic, biochemical or other methods. For example, an exogenous nucleic acid sequence can be part of an infecting viral vector, a plasmid, or an episome introduced into a cell. An additional example is of an exogenous nucleic acid sequence is a mammalian polynucleotide introduced into a virus polynucleotide sequence. Another example of an exogenous nucleic acid sequence or polypeptide is a nucleic acid sequence or polypeptide introduced to a cell that is not normally expressed at a detectable level in a comparable cell, or is a mutant and/or truncated form of a wild type polynucleotide or polypeptide.

The term "antigen" as used herein refers to a molecule that contains one or more epitopes capable of being bound by one or more MHC receptors, antibodies, or other antigen binding moieties. For example, an antigen can stimulate a host's immune system to make a cellular antigen-specific immune response when the antigen is presented. An antigen can also have the ability to elicit a cellular immune response by itself or when present in combination with another molecule. For example, a tumor cell antigen can be recognized by a T cell receptor (TCR). An antigen may be a wild type, mutant, or truncated version of a protein. Furthermore, antigens can be derived from recombinant or genomic DNA. It is recognized in the art that expressed DNA that contains nucleotide sequences or partial nucleotide sequences of the genome of a pathogenic organism or a gene or a fragment of a gene for a protein that elicits an immune response results in synthesis of an antigen. Furthermore, the present disclosure is not limited to the use of the entire nucleic acid sequence of a gene or cDNA. Accordingly, use of partial nucleic acid sequences of more than one gene or cDNA is contemplated herein and these nucleic acid sequences are arranged in various combinations to elicit the desired immune response.

The term "antigen-presenting cell" or "APC" is any of a variety of cells capable of displaying, acquiring, or presenting at least one antigen or antigenic fragment on (or at) its cell surface. Such cells can be identified using methods disclosed herein and known in the art. As is understood by one of ordinary skill in the art, and used herein certain embodiments, a cell that displays or presents an antigen with, for example, a class II major histocompatibility molecule or complex (MHCII) to an immune cell is an antigen-presenting cell.

As used herein, a "CD14 positive" or "CD14$^+$" cell refers to a cell that naturally expresses the CD14 gene. Examples of CD14$^+$ cells include monocytes, DC, and macrophages. Any method for detection of gene expression known in the art can be used to detect CD14 expression, such as flow cytometry, immunohistochemical staining, fluorescence microscopy, western blot, northern blot, and reverse transcription PCR. A cell population "positive" for a marker, as detected by flow cytometry, refers to uniform monoclonal antibody staining of the cell population above the levels found for staining with an isotype control. In some embodiments, an at least 2-fold increase in the MFI relative to the reference population indicates the cells are positive for expression of the marker. For example, a cell population that is positive for a marker can demonstrate a 2-fold to 4 fold, 4 fold to 10 fold, 10 fold to 100 fold, and 100 fold to 1,000 fold, 1,000 fold to 10,000 fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 50-fold, 100-fold, 200-fold, 300-fold, 400-fold, 500-fold, 600-fold, 700-fold, 800-fold, 900-fold, 1,000-fold, 5,000-fold, 10,000-fold or more higher MFI compared to an isotype control.

A "monocyte" is an immune cell that expresses the marker CD14 and is capable of differentiating into a dendritic cell or a macrophage. In addition to CD14, monocytes express at least one of CD11b, CCR2, and CD16.

A "dendritic cell" or "DC" is an antigen presenting cell existing in vivo, in vitro, ex vivo, or in a host or subject, or which can be derived from a monocyte or a hematopoietic stem cell. Dendritic cells and their precursors can be isolated from peripheral blood and bone marrow as well as a variety of lymphoid organs, e.g., spleen, lymph nodes. The DC has a characteristic morphology with thin sheets (lamellipodia) extending in multiple directions away from the dendritic cell body. DCs are potent professional antigen presenting cells for both MHC Class II as well as MHC Class I restricted systems (Santambrogio et al., PNAS 96(26):15050-55, 1999). Typically, dendritic cells express high levels of MHC and costimulatory (e.g., B7-1 and B7-2) molecules. Dendritic cells can induce antigen specific differentiation of T cells and are able to initiate cytotoxic T lymphocyte responses in vitro and in vivo.

As used herein, the term "differentiating cytokine" refers to a cytokine that is capable of promoting the differentiation of a monocyte into a dendritic cell. Examples of differentiating cytokines include, but are not limited to, GM-CSF, IL-4, and TNF-α.

As used herein, the term "activating cytokine" refers to a cytokine that is capable of promoting the activation of antigen specific T lymphocytes, such as cytotoxic T lymphocytes. Examples of activating cytokines include, but are not limited to, IL-2 and IL-7.

The terms "cancer" and "tumor" are used interchangeably herein and refer to a hyperproliferation of cells that results in unregulated growth, lack of differentiation, local tissue invasion, and/or metastasis.

As used herein, terms "treatment," "treat," "treated," or "treating" can include reversing, alleviating, inhibiting the progression of preventing or reducing the likelihood of the disease, disorder, or condition to which such term applies. When used with respect to a cancer, for example, the terms generally refer to reversing, alleviating, inhibiting the progression of disease and/or symptoms. When used with respect to an infectious disease, for example, the term can refer to treatment after the subject has become infected in order to fight the infection, e.g., reduce or eliminate the infection or prevent it from becoming worse, as well as a prophylactic treatment that increases the resistance of a subject to infection with a pathogen or, in other words, decreases the likelihood that will show signs of illness attributable to the infection.

An "effective amount" or "therapeutically effective amount" refers to that amount of a composition described herein which, when administered to a subject (e.g., human), is sufficient to aid in treating a disease. The amount of a composition that constitutes a "therapeutically effective amount" will vary depending on the cell and/or rAAV preparations, the condition and its severity, the manner of administration, and the weight and age of the subject to be treated, but can be determined routinely by one of ordinary skill in the art having regard to their own knowledge and to this disclosure.

As used herein, the term "induce an immune response" refers to the ability to activate and/or promote the antigen-specific, cell mediated immune response. For example, compositions of the present disclosure is capable of enhancing and/or activating the immune response. An immune response can be induced ex vivo and/or in vivo.

As used herein, "subject" or "patient" refers to one or more individuals that are in need of receiving treatment, therapy, cellular compositions, and/or rAAV compositions disclosed herein. Subjects that can be treated according to the present disclosure are, in general, human. However, additional subjects include a non-human primate, cow, horse, sheep, goat, pig, dog, cat, mouse, rabbit, rat, or Guinea pig. The subjects can be male or female and can be any suitable age, including infant, juvenile, adolescent, adult, and geriatric subjects.

As used herein, the term "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

As used herein, "sample" refers to a cell source (e.g. biological tissue) from which a population of cells may be isolated, enriched, or depleted. In some embodiments, a sample has generally not been previously processed or has been minimally processed. For example, the sample may be non-mobilized blood, non-mobilized apheresis product, mobilized peripheral blood, mobilized apheresis product, bone marrow, umbilical cord blood, peripheral blood mononuclear cells (PBMCs), or any combination thereof. In some embodiments, the sample is prepared or minimally processed by processing with a density gradient, Ficoll, Percoll, red blood cell hypotonic lysis, Ammonium-Chloride-Potassium (ACK) buffer, washed into a pH balanced isotonic buffer, or any combination thereof. In some embodiments, the sample is provided by a single tissue harvest. In some embodiments, the sample is provided by one or more tissue harvests.

Recombinant AAV Vectors

The AAV vectors provided herein have been engineered to deliver genes of interest by deleting the internal nonrepeating portion of the AAV genome by deleting the internal Cap and Rep genes and other endogenous DNA sections and inserting an exogenous nucleic acid sequence between the ITRs. The exogenous gene is operably linked to a CD14 promoter, which is capable of driving specific expression in a CD14-expressing (CD14$^+$) target cells. Accordingly, the present disclosure provides a polynucleotide comprising a recombinant adeno-associated virus (rAAV) vector encoding two ITR sequences and a CD14 promoter operably linked to an exogenous nucleic acid sequence, wherein the CD14 promoter induces specific expression of the exogenous nucleic acid in a CD14$^+$ cell. The CD14 promoter may be any mammalian CD14 promoter that will specifically drive expression of the exogenous nucleic acid sequence in a CD14 positive cell. In some embodiments, the CD14 promoter is a human CD14 promoter sequence. The human CD14 promoter comprises SEQ ID NO:1 or has at least 80%, 85%, 90%, 95%, 96%, 97%, 98%, or 99% sequence identity to SEQ ID NO:1, while being capable of driving specific expression in a CD14$^+$ cell. Referring to positions in SEQ ID NO:1, the CD14 promoter includes a TATA box (positions 481-486), a C/EBP site (positions 378-386), Sp1 binding sites (positions 404-410 and positions 533-538), Myb sites (positions 42-47 and positions 457-463), AP-1 sites (positions 113-121, positions 127-133, and positions 288-293), AP-2 sites (positions 276-283 and 356-364), and a CDP (CCATT displacement protein) site (positions 164-168). In certain embodiments, the CD14 promoter comprises a C/EBP site and a Sp1 site that regulate tissue-specific expression of CD14. In some embodiments, the CD14 promoter comprises at least the nucleotides at positions 378-386, positions 404-410 and positions 533-538 of SEQ ID NO:1. Examples of CD14 expressing cells include monocytes, dendritic cells, and macrophages.

In some embodiments, the rAAV vector includes, in the 5' to 3' direction, a first ITR, a CD14 promoter operably linked to the exogenous nucleic acid sequence, a polyadenylation signal sequence, and a second ITR. In some embodiments, the ITR sequences are AAV-2 ITR sequences or derived from AAV-2 ITR sequences. In some embodiments, the first ITR sequence and second ITR sequence are an AAV-2 ITR or derived from an AAV-2 ITR. In some embodiments, the ITR sequences are from any other AAV serotype, such as AAV1, AAV3, AAV4, AAV5, AAV6, AAV7, AAV8, AAV9 and AAVrh.10. Without wishing to be bound by theory, it is thought that the ITR sequences should be symmetrical for efficient multiplication of the sequence flanked by the first and second ITR. Examples of polyadenylation signal sequences include SV40 late polyadenylation signal, human growth hormone polyadenylation signal, and bovine growth hormone polyadenylation signal. In some embodiments, the rAAV vector further comprises an enhancer sequence. Enhancers are well known in the art and are genetic elements that increase transcription from a promoter. The enhancer sequence does not significantly affect the specificity of expression driven by the CD14 promoter. Examples of enhancers include, but are not limited to, simian virus 40 (SV40) enhancer, cytomegalovirus (CMV) immediate-early enhancer, and HACNS1 (CENTG2) enhancer.

In some embodiments, the rAAV vector is a plasmid vector, also referred to as "pAAV-CD14p" (i.e., a plasmid containing AAV ITR sequences and a CD14 promoter). In some embodiments, a plasmid vector comprises a human CD14 transcription promoter, AAV type 2 inverted terminal repeat (ITR) sequences, a multiple cloning site sequence (MCS), SV40 late poly-A sequence, an antibiotic resistance gene, such as beta lactamase gene (Ampicillin resistance gene, Amp$^r$), and gene elements that enable the plasmid to replicate in *E. coli* (such as DH5a). An exemplary plasmid vector is depicted in FIG. 1. In some embodiments, the plasmid comprises the sequence of SEQ ID NO:2. In some embodiments, the rAAV vector is encapsidated in an AAV virion.

In certain embodiments, the exogenous nucleic acid sequence comprises a multiple cloning site (MCS). MCS sequences are well known in the art, and also sometimes referred to as a polylinker. MCS sequences are usually a short segment of DNA that contains several unique sequences known as restriction sites that can be targeted by restriction endonucleases (also known as restriction enzymes). The MCS may contain up to 1, 2, 3, 4, 5, 6, 7, 8, 9, 10, 11, 12, 13, 14, 15, 16, 17, 18, 19, 20, or more unique restriction sites. Any restriction site known in the art may be used. Examples of restriction sites include AbsI, AscI, AvrII, BclI, BstZ17I, BstBI, Bst98I, BmgBI, BglII, ClaI, FseI, MluI, MreI, NdeI, NheI, NsiI, SnaBI, EcoRI, EcoRII, BamHI, HindIII, TaqI, NotI, HinFI, Sau3AI, PvuII, SmaI, HaeIII, HgaI, AluI, EcoRV, EcoP15I, KpnI, PstI, PmeI, RsrII, SacI, SalI, ScaI, SpeI, SphI, StuI, SgrDI, SrfI, XhoI, and XbaI. Additional restriction sites and restriction enzymes are listed in the REBASE database, which is hereby incorporated by reference in its entirety.

In some embodiments, the exogenous nucleic acid sequence comprises a sequence encoding an RNA and/or polypeptide. In certain embodiments, the sequence encoding an RNA and/or polypeptide is inserted into the MCS. Examples of the RNA include mRNA, short interfering RNA (siRNA), short-hairpin RNA (shRNA), micro-RNA (miRNA), and ribozymes. In some embodiments, the exogenous nucleic acid sequence encodes an antigenic polypeptide. Example of antigenic polypeptides include a tumor antigen, tumor-associated antigen, oncogene product, viral antigen, bacterial antigen, or any combination thereof. In certain embodiments, the antigenic polypeptide may be a full-length protein, an antigenic fragment of the protein, a truncated protein, and/or a mutant form of a protein.

Cells, including dendritic cells, naturally produce a repertoire of peptides from essentially any cellular translation product (e.g., protein) and present the peptides on the surface of the cell via peptide/MHC complexes. Proteolysis of endogenous and/or exogenous proteins produces smaller peptides that may be bound to MHC molecules to form a peptide/MHC complex. The peptide/MHC complex is then trafficked to the cell surface. T cell receptors (TCRs) on the surface of circulating cytotoxic T cells probe the peptide/MHC complexes for the presence of peptides, such as tumor antigens or viral proteins, which triggers a T cell directed immune response. The cellular processes for production and presentation of peptides on the surface of cells have been summarized in, for example, "Janeway's Immunobiology" $9^{th}$ Ed. (2016).

In some embodiments, the tumor antigen, tumor-associated antigen, or oncogene product may be any such antigenic polypeptide or fragment thereof known in the art. Examples of tumor antigens, tumor-associated antigens, or oncogene products include, but are not limited to, an alpha fetoprotein (AFP), B melanoma antigen (BAGE/CT2.1), Cluster of Differentiation 20 (CD20), CD269, G250 (carbonic anhydrase IX/CA IX), HM1.24, CD154, prostate cancer-associated antigens (such as prostate specific antigen (PSA), prostate specific membrane antigen (PSMA), prostate stem cell antigen (PSCA) and prostatic acid phosphatase (PAP) antigen), breast cancer-related tumor associated antigens (such as breast epithelial antigen 46 (BA46, lactadherin)), cancer-testis antigen (CT) family (such as New York Esophageal Squamous Cell Carcinoma-1 (NY-ESO-1) (CT6.1), ADAM2 (CT15), SPA17 (SP17, CT22), SPANX, e.g., Spanx-A1 (CT11.1)), human melanoma-associated antigen (MAGE) family (such as MAGE-A1/CT1.1, MAGE-A2/CT1.2, MAGE-A3/CT1.3, MAGE-A4/CT1.4, MAGE-B1/CT3.1, MAGE-C1/CT7.1, MAGE-C2/CT10, MAGE-C3/CT7.2, MAGE-E1), MART 1, SAGE 1, carcinoembryonic antigen (CEA), HER-2/neu, cytokeratin 19 (CK19, K19, cyfra21-1), Survivin, Mucin-1 (MUC-1, CA15-3), Squamous cell carcinoma (SCC) antigen, or any antigenic fragment and/or combination thereof.

In some embodiments, the viral antigen may be any viral antigen known in the art. Examples of viral antigens include, but are not limited to, a hepatitis B virus (HBV) antigen, hepatitis C virus (HCV) antigen, human papilloma virus (HPV) antigen, human immunodeficiency virus (HIV) antigen, cytomegalovirus (CMV), Epstein-Barr virus (EBV), influenza virus, parainfluenza viruses, respiratory syncytial virus (RSV), herpes simplex viruses (HSV), papillomavirus, measles virus, rotavirus, or any antigenic fragment and/or combination thereof. In some embodiments, the HPV antigen is an E6 polypeptide, an E7 polypeptide, or any antigenic fragment thereof. In certain embodiments, exogenous nucleic acid sequence comprises a sequence encoding an E6 polypeptide and an E7 polypeptide, or antigenic fragments thereof. In certain embodiments, the E6 or E7 antigen is derived from HPV serotype 16, 18, 30, 31, 33, 35, 39, 45, 51, 52, 56, 58, 61, or any antigenic fragment and/or combination thereof. In some embodiments, the HBV antigen is HBsAg, HBeAg, HBcAg and/or HBxAg. In some embodiments, the HCV antigen is a C, E1, E2, NS1, NS2, NS3, NS4 and/or NS5 antigen. In some embodiments, the HIV antigen is a gag antigen, pol antigen and/or env antigen. In some embodiments, the CMV antigen is a pp65 antigen, pp150 antigen, and/or gB antigen. In some embodiments, the EBV antigen is a LMP-1 antigen, LMP-2A antigen, LMP-2B antigen, EAR antigen, EAD antigen, VCA antigen, MA antigen, EBNA1 antigen, EBNA2 antigen, EBNA3 antigen, EBNA3B antigen, and/or EBNA3C antigen.

In some embodiments, the bacterial antigen may be any bacterial antigen known in the art. Examples of bacteria from which the bacterial antigen may be derived include, but are not limited to, *Mycobacterium tuberculosis*, Helicobacters, Campylobacters, Clostridia, *Corynebacterium diphtheriae, Bordetella pertussis, Borrelia burgdorferi*, Plasmodium, *Vibrio cholera, Escherichia coli*, Shigella, *Salmonella typhi*, and *Neisseria gonorrhea*. In certain embodiments, the *Mycobacterium tuberculosis* antigen is a MPT44 antigen, MPT45 antigen, MPT59 antigen, MPT64 antigen, Ag85B antigen, Rv3117 antigen, and/or ESAT-6 antigen.

Table 1 provides a list of representative antigens and the UniProtUK accession numbers available at the time of filing. The version number refers to the version of the sequence provided in the database. Also provided are UniProtUK accession numbers for known and predicted isoforms.

TABLE 1

Representative Antigens and Corresponding UniProtUK Accession Numbers.

| Antigen | UniProtUK Accession No. |
|---|---|
| AFP | P02771 version 1 |
| BAGE/CT2.1 | Q13072 version 1, Q13072-1, Q13072-2, Q13072-3, Q13072-4, Q13072-5, Q13072-6 |
| CD20 | P11836 version 1, P1836-1, P11836-2, E9PPL6, E9PKH8 |
| CD269 | Q02223 version 2, Q02223-1, Q02223-2 |
| G250 | Q16790 version 2, Q16790-1 |
| HM1.24 | Q10589 version 1, Q10589-1, Q10589-2 |
| CD154 | P29965 version 1, P29965-1, Q3L8U2 |
| PSA | P07288 version 2, P07288-1, P07288-2, P07288-3, P07288-4, P07288-5, Q8WTQ8, Q8NCW4, M0R294, M0R1F0, M0QZF9, M0R1Z7, M0QX57, A0A0B4J1X3 |
| PSMA | Q04609 version 1, Q04609-1, Q04609-2, Q04609-3, Q04609-4, Q04609-5, Q04609-6, Q04609-7, Q04609-8, Q04609-9, Q04609-10 |
| PSCA | O43653 version 2, O43653-1, H0YAA6 |
| PAP | P15309 version 3, P15309-1, P15309-2, P15309-3 |
| BA46 | Q08431 version 3, Q08431-1, Q08431-2, Q08431-3, Q08431-4 |
| NY-ESO-1/CT6.1 | P78358 version 1, P78358-1, P78358-2 |
| ADAM2/CT15 | Q99965 version 2, Q99965-1, Q99965-2 |
| SPA17/CT22 | Q15506 version 1 |
| SPANX/CT11.1 | Q9NS26 version 1 |
| MAGE-A1/CT1.1 | P43355 version 1 |
| MAGE-A2/CT1.2 | P43356 version 1, P43356-1 |
| MAGE-A3/CT1.3 | P43357 version 1, P43357-1 |
| MAGE-A4/CT1.4 | P43358 version 2, P43358-1 |
| MAGE-B1/CT3.1 | P43366 version 2 |
| MAGE-C1/CT7.1 | O60732 version 3, O60732-1, O60732-2 |
| MAGE-C2/CT10 | Q9UBF1 version 1 |
| MAGE-C3/CT7.2 | Q8TD91 version 1, Q8TD91-1, Q8TD91-2 |
| MAGE-E1 | Q9HCI5 version 2 |
| MART 1 | Q16655 version 1 |
| SAGE 1 | Q9NXZ1 version 2, Q9NXZ1-1 |
| CEA | P06731 version 3, P06731-1, P06731-2 |
| HER-2/neu | P04626 version 1, P04626-1, P04626-2, P04626-3, P04626-4, P04626-5, P04626-6 |
| CK19 | P08727 version 4, P08727-1, P08727-2 |
| Survivin | O15392 version 3, O15392-1, O15392-2, O15392-3, O15392-4, O15392-5, O15392-6, O15392-7 |
| MUC-1/CA15-3 | P15941 version 3, P15941-1, P15941-2, P15941-3, P15941-4, P15941-5, P15941-6, P15941-7, P15941-8, P159419, P15941-10, P15941-11, P15941-12, P15941-13, P15941-14, P15941-15. P15941-16. P15941-17 |
| SCC | P29508 version 2, P29508-1, P29508-2 |
| HPV-E6 | P03126 version 1, P06463 version 1 |
| HPV-E7 | P03129 version 1, P06788 version 2, |
| EBV LMP-1 | P03230 version 1, A0A0C7SWW3 version 1, A0A7H0XLW7 version 1, A8CSJ8 version 1 |

In some embodiments, the exogenous nucleic acid sequence encodes a cytokine. The cytokine may be an interleukin, interferon, tumor necrosis factor, Granulocyte Macrophage Colony-Stimulating Factor (GM-CSF), or any combination thereof. Examples of cytokines include, but are not limited to, GM-CSF, TNF-α, IL-4, IL-7, IL-12, IL-15, IL-18, TGF-β, other Th1 cytokines known in the art, such as IFNγ, IL-2, IL-10, IL-18, and IL-27, other Th2 cytokines known in the art, such as IL-5, IL-9, IL-10, IL-13, IL-25, and amphiregulin, and/or any combination thereof.

In certain embodiments, the rAAV vector further includes internal ribosome entry sites (IRES) sequences. IRES sequences can be used to create multigene or polycistronic messages. IRES sequences can be operably linked to exogenous nucleic acid sequences that encode RNA and/or polypeptides. Multiple exogenous nucleic acid sequences can be transcribed together, each separated by an IRES, creating polycistronic messages. By virtue of the IRES sequence, each open reading frame is accessible to ribosomes for efficient translation. Multiple genes can be efficiently expressed using a single promoter to transcribe a single message encoding at least two RNAs and/or polypeptides (see U.S. Pat. Nos. 5,925,565 and 5,935,819, each herein incorporated by reference).

According to the instant disclosure, rAAV plasmid vectors are named according to the formula "pAAV-[promoter]/[payload]." Therefore, "pAAV-CD14p/exogenous gene" refers to an rAAV plasmid vector comprising a CD14 promoter operably linked to an exogenous nucleic acid sequence, wherein the CD14 promoter and the exogenous nucleic acid sequence are flanked by ITR sequences located at 5' and 3' regions of the sequence. Additional examples include, pAAV-CD14p/antigen and pAAV-CD14p/cytokine, which refer to rAAV plasmid vectors, wherein the CD14 promoter is operatively linked to a nucleic acid sequence encoding an antigen or a cytokine, respectively. In addition, rAAV plasmid vectors that include exogenous sequences encoding particular polypeptides include the name of the exogenous sequence. For example, an rAAV plasmid vector comprising a CD14 promoter operably linked to an exogenous nucleic acid encoding PSA is referred to as "pAAV-CD14p/PSA." Examples of rAAV plasmid vectors include, pAAV-CD14p/AFP, pAAV-CD14p/BA46, pAAV-CD14p/CT2.1, pAAV-CD14p/CEA, pAAV-CD14p/CD20, pAAV- CD14p/CD269, pAAV-CD14p/CK19, pAAV-CD14p/G250, pAAV-CD14p/HPV16-E6, pAAV-CD14p/HPV16-E7, pAAV-CD14p/HPV16-E6-E7, pAAV-CD14p/HPV18-E6, pAAV-CD14p/HPV18-E7, pAAV-CD14p/HPV18-E6-E7, pAAV-CD14p/HER2, pAAV-CD14p/HM1.24, pAAV-CD14p/LMP-1, pAAV-CD14p/MAGE-A1, pAAV-CD14p/MAGE-A2, pAAV-CD14p/MAGE-A4, pAAV-CD14p/MAGE-B1, pAAV-CD14p/MAGE-C1, pAAV-CD14p/MAGE-E1, pAAV-CD14p/MART1, pAAV-CD14p/MUC-1, pAAV-CD14p/CT6.1, pAAV-CD14p/PSA, pAAV-CD14p/PAP, pAAV-CD14p/PSMA, pAAV-CD14p/PSCA, pAAV-CD14p/SAGE1, pAAV-CD14p/SCC, pAAV-CD14p/SPANX, pAAV-CD14p/SPA17, and pAAV-CD14p/Survivin.

rAAV Virions

In certain embodiments, disclosed herein is an rAAV virion comprising a CD14 promoter operably linked to an exogenous nucleic acid sequence, wherein the CD14 promoter induces expression of the exogenous nucleic acid specifically in a $CD14^+$ cell. The rAAV virion can comprise any of the polynucleotide sequences disclosed in the embodiments and examples provided herein. In some embodiments, the rAAV virion comprises nucleic acid sequences encoding an antigenic polypeptide, such as any of the tumor antigens, tumor-associated antigens, oncogene products, viral antigens, bacterial antigens, or any combinations thereof as disclosed herein. In some embodiments, the rAAV virion comprises capsid proteins of AAV1, AAV2, AAV3, AAV4, AAV5, AAV6, AAV7, AAV8, AAV9, AAV10, AAVrh.10, AAV11, or any combination thereof. In certain embodiments, the rAAV virion comprises capsid proteins of AAV2, AAV3, AAV5, AAV6, or any combination thereof. In certain embodiments, the rAAV virion comprises capsid proteins of AAV2. In some embodiments, a chimeric rAAV virion is used wherein the viral origins of the ITR sequences of the rAAV vector are heterologous to the viral origin of the capsid sequences. Examples include chimeric virus with ITR derived from AAV2 and capsids derived from AAV5, AAV6, AAV8 or AAV9 (i.e., AAV2/5, AAV2/6, AAV2/8 and AAV2/9, respectively). In certain embodiments, the rAAV virion does not comprise promoters other than the CD14 promoter. In certain embodiments, the rAAV virion does not include AAV structural genes, i.e., Rep and/or Cap genes. According to the instant disclosure, rAAV virions are named according to the formula "rAAV-[promoter]/[payload]." Examples of rAAV virions include, rAAV-CD14p/AFP, rAAV-CD14p/BA46, rAAV-CD14p/CT2.1, rAAV-CD14p/CEA, rAAV-CD14p/CD20, rAAV-CD14p/CD269, rAAV-CD14p/CK19, rAAV-CD14p/G250, rAAV-CD14p/HPV16-E6, rAAV-CD14p/HPV16-E7, rAAV-CD14p/HPV16-E6-E7, rAAV-CD14p/HPV18-E6, rAAV-CD14p/HPV18-E7, rAAV-CD14p/HPV18-E6-E7, rAAV-CD14p/HER2, rAAV-CD14p/HM1.24, rAAV-CD14p/LMP-1, rAAV-CD14p/MAGE-A1, rAAV-CD14p/MAGE-A2, rAAV-CD14p/MAGE-A4, rAAV-CD14p/MAGE-B1, rAAV-CD14p/MAGE-C1, rAAV-CD14p/MAGE-E1, rAAV-CD14p/MART1, rAAV-CD14p/MUC-1, rAAV-CD14p/CT6.1, rAAV-CD14p/PSA, rAAV-CD14p/PAP, rAAV-CD14p/PSMA, rAAV-CD14p/PSCA, rAAV-CD14p/SAGE1, rAAV-CD14p/SCC, rAAV-CD14p/SPANX, rAAV-CD14p/SPA17, and rAAV-CD14p/Survivin.

In one aspect disclosed herein are methods of producing an rAAV virion, comprising introducing a pAAV-CD14p/exogenous plasmid into a packaging cell, wherein the packaging cell comprises one or more nucleic acid sequences encoding helper genes. To produce infectious rAAV virions, a suitable packaging cell line may be transfected with a plasmid comprising any of the rAAV vectors disclose in the embodiments and examples herein. The packaging cell line contains a helper plasmid encoding the other AAV genes, i.e., Rep and Cap, but lacking ITR sequences. The packaging cell line also contains a plasmid encoding helper virus genes, e.g., adenovirus genes that are required for production of infectious virions. For example, the helper plasmid may comprise VA, E2A, E3 and E4 genes of adenovirus, e.g., adenovirus type 5. The helper virus genes promote replication of the rAAV vector and expression of AAV genes from the helper plasmid. The helper plasmid is not packaged in significant amounts due to a lack of ITR sequences. In certain embodiments, the helper genes are included on a single plasmid. In other embodiments, the helper genes are included on more than one plasmid (e.g., two plasmids). In some embodiments, the pAAV-CD14p/exogenous plasmid is co-transfected into a packaging cell with one or more plasmids comprising the helper genes. Alternatively, packaging cell line may also be infected with adenovirus as a helper. In some embodiments, the pAAV-CD14p/exogenous plasmid is co-transfected into a packaging cell with a plasmid comprising the Rep and Cap genes and the cell is infected with an adenovirus. Contamination with adenovirus can be reduced by, e.g., heat treatment to which adenovirus is more sensitive than AAV. In some embodiments, the packaging cell is a mammalian cell. Examples of packaging cells that can be used to produce rAAV virions include, but are not limited to, HEK 293, HeLa, and HT1080 cells. In some embodiments, the packaging cell is a HEK 293T cell. The packaging cell line can also be stably transfected or transduced with one or more vectors comprising the AAV Rep and Cap genes and adenoviral VA, E2A, E3 and E4 genes. Additional methods for the delivery of polynucleotides to cells are known in the art. The rAAV virions disclosed herein cannot replicate to form progeny infectious virions in target cells (e.g., monocytes and DC) because the target cells lack the Rep and Cap genes and the adenovirus helper genes.

Methods of Producing Modified Antigen Presenting Cells and Producing Antigen-Specific T Cells Disclosed herein are methods of using the rAAV vectors provided herein to specifically express exogenous nucleic acid sequences in $CD14^+$ target cells. In some embodiments is a method of producing a modified APC, comprising: i) providing a $CD14^+$ cell; ii) contacting the $CD14^+$ cell with any of the rAAV vectors disclosed herein, in an amount sufficient to express an exogenous nucleic acid sequence encoding a polypeptide; and iii) culturing the $CD14^+$ cell of step ii) for a time sufficient to express the polypeptide. The $CD14^+$ cell can be a monocyte or a dendritic cell. The rAAV vector may be an rAAV virion or an rAAV plasmid disclosed in any of the embodiments herein. The $CD14^+$ cell may be contacted with the rAAV virion by co-culturing the $CD14^+$ cell with the rAAV virion for a time sufficient for the rAAV virion to transduce the $CD14^+$ cell. Alternatively, the $CD14^+$ cell can be transfected with an rAAV plasmid.

In some embodiments, the monocyte is in a population of peripheral blood mononuclear cells (PBMC). In some embodiments, the monocyte is an isolated monocyte. In some embodiments, the isolated monocyte is isolated from a sample. In some embodiments, the isolated monocyte is isolated from a population of PBMC. The monocyte can be isolated from the population of PBMC using any method known in the art. For example, PBMC can be obtained from a blood sample by density gradient centrifugation. Monocytes can then be sorted using anti-CD14 antibodies (and/or other suitable monocyte markers) linked to a tag, label, or bead. The monocytes are then sorted or isolated using, for example, fluorescence activated cell sorting (FACS) or magnetic bead separation. Alternatively, monocytes can be separated from PBMC using anti-CD3 antibodies to sort and remove non-monocytes from the PBMC sample. Monocytes may also be separated from CD3$^+$ lymphocytes using adherent culture separation techniques known in the art.

In some embodiments, step ii) above further comprises differentiating the monocyte into a dendritic cell. In some embodiments, the monocyte is differentiated into a dendritic cell by contacting the monocyte with a cytokine for a time sufficient to differentiate the monocyte into a dendritic cell. In some embodiments, the cytokine is added to the cell culture. In some embodiments, the monocyte is differentiated into a dendritic cell by introducing a polynucleotide encoding an exogenous cytokine into the monocyte, thereby causing the monocyte to express the exogenous cytokine. The nucleic acid encoding the exogenous cytokine can be a plasmid or rAAV virion. In some embodiments, the nucleic acid encoding the exogenous cytokine is operably linked to a CD14 promoter. The cytokine added to the media or encoded in the nucleic acid sequence can be GM-CSF, IL-4, TNF-α, or any combination thereof. The time sufficient to differentiate the monocyte into a dendritic cell can be readily determined a person of skill in the art. In some embodiments, the time sufficient to differentiate the monocyte into a dendritic cell is between 1 and 8 days, between 2 and 7 days, or between 3 and 6 days. In some embodiments, the time sufficient to differentiate the monocyte into a dendritic cell is at least 1 day, 2 days, 3 days, 4 days, 5 days, 6 days, 7 days, or 8 days. In addition, any of the methods for differentiating a monocyte into a dendritic cell known in the art may be used.

Also provided herein are methods of producing antigen-specific T cells. In some embodiments the method of producing an antigen-specific T cell comprises: i) providing a naïve T cell; ii) contacting the naïve T cell with any the modified APC described in the embodiments and examples herein; and iii) contacting the T cell of step ii) with an activating cytokine. Preferably, the modified APC is a modified dendritic cell specifically expressing an exogenous nucleic acid encoding an antigenic polypeptide. The activating cytokine can be added to T cells in the culture media. The activating cytokine can be IL-2, IL-7, or both. In some embodiments, the antigen-specific T cell is a CD4$^+$ T cell, a CD8$^+$ T cell, or a mixture thereof. In some embodiments, the modified dendritic cell further comprises an rAAV vector comprising a CD14 promoter operatively linked to a nucleic acid sequence encoding IL-12 and expresses IL-12 polypeptide, thereby enhancing CD8$^+$ T cell proliferation.

In some embodiments, the method of producing antigen-specific T cells comprises: i) providing a population of PBMC comprising CD14$^+$ monocytes and CD3$^+$ T cells; ii) contacting the population of PBMC with any of the rAAV vectors disclosed in the embodiments and examples herein, in an amount sufficient to express an exogenous nucleic acid sequence encoding a polypeptide; iii) differentiating monocytes in the PBMC into dendritic cells by contacting the monocytes with a cytokine and culturing the monocytes for a time sufficient to differentiate into dendritic cells; and iv) contacting the differentiated dendritic cells and CD3$^+$ T cells with an activating cytokine and culturing the differentiated dendritic cells and CD3$^+$ T cells for time sufficient to produce antigen specific T cells. In some embodiments, the monocytes are differentiated into dendritic cell by contacting the monocytes with a cytokine. The cytokine can be GM-CSF, IL-4, TNF-α, or any combination thereof. In some embodiments, the time sufficient to differentiate the monocyte into a dendritic is between 1 and 8 days, between 2 and 7 days, or between 3 and 6 days. In some embodiments, the time sufficient to differentiate the monocyte into a dendritic is at least 1 day, 2 days, 3 days, 4 days, 5 days, 6 days, 7 days, or 8 days. The activating cytokine can be IL-2, IL-7, or both. In some embodiments, the time sufficient to produce antigen specific T cells by culturing the differentiated dendritic cells and CD3$^+$ T cells is between 1 and 12 days, between 2 and 10 days, or between 3 and 6 days. In some embodiments, the time sufficient to produce antigen specific T cells by culturing the differentiated dendritic cells and CD3$^+$ T cells is at least 1 day, 2 days, 3 days, 4 days, 5 days, 6 days, 7 days, 8 days, 9 days, 10 days, 11 days, or 12 days. The antigen-specific T cells can be CD4$^+$ T cells, CD8$^+$ T cells, or a mixture thereof.

Pharmaceutical Compositions and Methods of Treatment

Also provided herein are pharmaceutical compositions and methods of treatment of diseases. In some embodiments, provided herein is a pharmaceutical composition comprising a population of modified APC, wherein the modified APC is any of the modified APC disclosed in the embodiments and examples herein, and is effective to activate T cells to produce an antigen-specific immune response against a polypeptide encoded by an exogenous nucleic acid sequence operably linked to a CD14 promoter; and a pharmaceutically acceptable carrier. The modified APC can be monocytes, dendritic cells, or a combination thereof. In some embodiments, the modified APC is a dendritic cell that was differentiated from a monocyte. In some embodiments, the modified APC is an isolated monocyte. In some embodiments, the modified APC is an isolated dendritic cell. In some embodiments, the modified APC is in a mixture of PBMC. In some embodiments, the modified APC is in a mixture with CD3$^+$ T cells. In some embodiments, the pharmaceutical composition comprises a mixture of modified APC and antigen-specific T cells. In some embodiments, the antigen-specific T cells are CD4+ T cells, CD8+ T cells, or a mixture thereof.

In some embodiments, the modified APC of the pharmaceutical composition specifically express a tumor antigen, tumor-associated antigen, oncogene product, viral antigen, or bacterial antigen.

In some embodiments, the tumor antigen, tumor-associated antigen, or oncogene product may be any such antigenic polypeptide or fragment thereof known in the art. Examples of tumor antigens, tumor-associated antigens, or oncogene products include, but are not limited to, an alpha fetoprotein (AFP), B melanoma antigen (BAGE/CT2.1), Cluster of Differentiation 20 (CD20), CD269, G250 (carbonic anhydrase IX/CA IX), HM1.24, CD154, prostate cancer-associated antigens (such as prostate specific antigen (PSA), prostate specific membrane antigen (PSMA), prostate stem cell antigen (PSCA) and prostatic acid phosphatase (PAP) antigen), breast cancer-related tumor associated antigens (such as breast epithelial antigen 46 (BA46, lactadherin)), cancer-testis antigen (CT) family (such as New York Esophageal Squamous Cell Carcinoma-1 (NY-ESO-1) (CT6.1), ADAM2 (CT15), SPA17 (SP17, CT22), SPANX, e.g., Spanx-A1 (CT11.1)), human melanoma-associated antigen (MAGE) family (such as MAGE-A1/CT1.1, MAGE-A2/CT1.2, MAGE-A3/CT1.3, MAGE-A4/CT1.4, MAGE-B1/CT3.1, MAGE-C1/CT7.1, MAGE-C2/CT10, MAGE-C3/CT7.2, MAGE-E1), MART 1, SAGE 1, carcinoembryonic antigen (CEA), HER-2/neu, cytokeratin 19 (CK19, K19, cyfra21-1), Survivin, Mucin-1 (MUC-1, CA15-3), Squamous cell carcinoma (SCC) antigen, or any antigenic fragment and/or combination thereof.

In some embodiments, the viral antigen may any viral antigen known in the art. Examples of viral antigens include, but are not limited to, a hepatitis B virus (HBV) antigen, hepatitis C virus (HCV) antigen, human papilloma virus (HPV) antigen, human immunodeficiency virus (HIV) antigen, influenza virus, parainfluenza viruses, respiratory syncytial virus (RSV), cytomegalovirus (CMV), Epstein-Barr virus (EBV), herpes simplex viruses (HSV), papillomavirus, measles virus, rotavirus, or any antigenic fragment and/or combination thereof. In some embodiments, the HPV antigen is an E6 polypeptide, an E7 polypeptide, or any antigenic fragment thereof. In certain embodiments, exogenous nucleic acid sequence comprises a sequence encoding an E6 polypeptide and an E7 polypeptide, or antigenic fragments thereof. In certain embodiments, the E6 or E7 antigen is derived from HPV serotype 16, 18, 30, 31, 33, 35, 39, 45, 51, 52, 56, 58, 61, or any antigenic fragment and/or combination thereof. In some embodiments, the HBV antigen is HBsAg, HBeAg, HBcAg and/or HBxAg. In some embodiments, the HCV antigen is a C, E1, E2, NS1, NS2, NS3, NS4 and/or NS5 antigen. In some embodiments, the HIV antigen is a gag antigen, pol antigen and/or env antigen. In some embodiments, the CMV antigen is a pp65 antigen, pp150 antigen, and/or gB antigen. In some embodiments, the EBV antigen is a LMP-1 antigen, LMP-2A antigen, LMP-2B antigen, EAR antigen, EAD antigen, VCA antigen, MA antigen, EBNA1 antigen, EBNA2 antigen, EBNA3 antigen, EBNA3B antigen, and/or EBNA3C antigen.

In some embodiments, the bacterial antigen may be any bacterial antigen known in the art. Examples of bacteria from which the bacterial antigen may be derived include, but are not limited to, *Mycobacterium tuberculosis*, Helicobacters, Campylobacters, Clostridia, *Corynebacterium diphtheriae*, *Bordetella pertussis*, *Borrelia burgdorferi*, Plasmodium, *Vibrio cholera*, *Escherichia coli*, Shigella, *Salmonella typhi*, and *Neisseria gonorrhea*. In certain embodiments, the *Mycobacterium tuberculosis* antigen is a MPT44 antigen, MPT45 antigen, MPT59 antigen, MPT64 antigen, Ag85B antigen, Rv3117 antigen, and/or ESAT-6 antigen.

In some embodiments, the exogenous nucleic acid sequence encodes a cytokine. The cytokine may be an interleukin, interferon, tumor necrosis factor, granulocyte Macrophage Colony-Stimulating Factor (GM-CSF), or any combination thereof. Examples of cytokines include, but are not limited to, GM-CSF, TNF-α, IL-12, IL-4, IL-7, IL-12, IL-15, IL-18, TGF-β, other Th1 cytokines known in the art, such as IFNγ, IL-2, IL-10, IL-18, and IL-27, other Th2 cytokines known in the art, such as IL-5, IL-9, IL-10, IL-13, IL-25, and amphiregulin, and/or any combination thereof.

The rAAV virions, modified APC, and activated T cells disclosed herein can be used to treat diseases and disorders. In some embodiments, provided herein is a method of immunotherapy, comprising administering an effective amount of any of the rAAV virions disclosed herein to a subject in need thereof, thereby stimulating an immune response. In some embodiments, provided is a method of immunotherapy, comprising administering an effective amount of any of the cells (e.g., isolated cells) comprising any of rAAV vectors disclosed herein and/or any of the pharmaceutical compositions disclosed herein to a subject in need thereof, thereby stimulating an immune response. In some embodiments, provided is a method of immunotherapy comprising administering an effective amount of a population of antigen specific T cells that were activated by any of the modified APC described herein and target cells expressing the antigen encoded by any of the rAAV vectors described herein. In some embodiments, provided is a method of immunotherapy comprising administering an effective amount of a population PBMC, wherein the PBMC comprise antigen specific T cells that were activated by any of the modified APC described herein and target cells expressing the antigen encoded by any of the rAAV vectors described herein. In some embodiments, the subject is a human. In some embodiments, the population of isolated cells was from a sample obtained from the subject to be treated or under treatment.

In some embodiments, peripheral venous blood may be collected from a patient (e.g., a cancer patient) to be treated and used to isolate peripheral blood mononuclear cells. The isolated peripheral blood mononuclear cells may be cultured in vitro (e.g., in a cell culture plate or petri dish), and monocytes in the peripheral blood mononuclear cells may be then separated from peripheral blood lymphocytes. The monocytes may then be infected by rAAV virions provided herein and subsequently differentiated into DCs in the presence of cytokine(s). After maturation (e.g., cultured for 6 days), DCs may be collected and added to the culture of peripheral blood lymphocytes prepared as described above to generate a mixed culture. After the mixed culture is cultured for a sufficient time (e.g., 6-12 days), cytotoxic T lymphocytes (CTLs) in the mixed culture may be harvested and administered to the patient (e.g., via intravenous administration).

In some related embodiments, peripheral venous blood may be collected from a patient (e.g., a cancer patient) to be treated and used to isolate peripheral blood mononuclear cells. The isolated peripheral blood mononuclear cells (PBMCs) may be infected by rAAV virions provided herein, and monocytes of the infected PBMCs may be subsequently differentiated into DCs in the presence of cytokines (e.g., GM-CSF, IL-4 and TNF-α). In addition, cytokines (e.g., IL-2 and IL7) may be added to the cultured PBMCs to activate CTLs. The resulting PBMCs comprising activated CTLs or activated CTLs harvested from the PBMCs may be then administered to the patient (e.g., via intravenous administration).

In some embodiments, the present disclosure provides a method of immunotherapy, comprising:

a. infecting peripheral blood mononuclear cells (PBMCs) of a subject with an rAAV virion provided herein to generate infected PBMCs, b. adding a differentiating cytokine (e.g., GM-CSF, IL-4 and TNF-α) to differentiate monocytes of the infected PBMCs into dendritic cells (DCs), c. adding an activating cytokine (e.g., IL-2 and IL7) to activate cytotoxic T lymphocytes (CTLs) of the infected PBMCs to generate activated CTLs, d. optionally isolating activated CTLs from the infected PBMCs, and e. administering an effective amount of the infected PMBCs that comprise activated CTLs or isolated activated CTLs to the subject.

In some embodiments, the subject in need thereof has been diagnosed with a cancer, tumor, viral infection, or bacterial infection.

In some embodiments, the cancer is acute lymphocytic cancer, acute myeloid leukemia, alveolar rhabdomyosarcoma, bladder cancer, bone cancer, brain cancer, breast cancer, cancer of the anus, anal canal, rectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and/or urinary bladder cancer. In some embodiments, the cancer is AFP-positive liver cancer; BA46-positive breast cancer; CT2.1-positive malignant melanoma lung cancers, gastric cancer, or other CT2.1-positive malignant cancers; CEA-positive lung cancer, colon cancer, breast cancer, or other CEA-positive cancers; CD20-positive malignant thymoma, lymphoma, myeloma and other CD20-positive sarcomas; CD269-positive liver cancer, CK19-positive lung cancer, colon cancer, breast cancer and other CK19-positive cancers; G250-positive malignant gastrointestinal tumors, kidney cancer, melanoma and other G250-positive cancers; HPV-16 E6-positive cervical cancer and other HPV-16 E6-positive malignant tumors; HPV-16 E7-positive cervical cancer and other HPV-16 E7-positive malignant tumors; HPV-16 E6 and E7-positive cervical cancer and other HPV-16 E6 and E7-positive malignant tumors; HPV-18 E6-positive cervical cancer and other HPV-18 E6-positive malignant tumors; HPV-18 E7-positive cervical cancer and other HPV-18 E7-positive malignant tumors; HPV-18 E6 and E7-positive cervical cancer and other HPV-18 E6 and E7-positive malignant tumors; HER2/neu-positive breast cancer, lung cancer, gastrointestinal tumors, kidney cancer, melanoma and other HER2/neu-positive malignant tumors; HM1.24-positive multiple myeloma, myeloma, and lymphoma; LMP-1-positive nasopharyngeal carcinoma and lymphoma; MAGE-A1-positive lung cancer, gastrointestinal tumors, kidney cancer, melanoma and other MAGE-A1-positive malignant tumors; MAGE-A2-positive lung cancer, gastrointestinal tumors, kidney cancer, melanoma and other MAGE-A2-positive malignant tumors; MAGE-A4-positive lung cancer, gastrointestinal tumors, kidney cancer, melanoma and other MAGE-A4-positive malignant tumors; MAGE-B1-positive lung cancer, gastrointestinal tumors, kidney cancer, melanoma and other MAGE-B1-positive malignant tumors; MAGE-C1-positive lung cancer, gastrointestinal tumors, kidney cancer, melanoma and other MAGE-C1-positive malignant tumors; MAGE-C1-positive lung cancer, gastrointestinal tumors, kidney cancer, melanoma and other MAGE-C1-positive malignant tumors; MART 1-positive melanoma and other MART 1-positive malignant tumors; MUC-1-positive malignant tumors; NY-ESO-1-positive malignant tumors; PSA-positive prostate cancer; PAP-positive prostate cancer; PSMA-positive prostate cancer, lung cancer, breast cancer, kidney cancer and other PSMA-positive malignant tumors; PSCA-positive prostate cancer; SAGE 1-positive sarcomas, melanoma and other SAGE 1 malignant tumors; SCC-positive squamous cell carcinomas; SPANX-A1-positive adenocarcinomas, sarcomas and melanoma; SPA17-positive adenocarcinomas, sarcomas and melanoma; and survivin-positive malignant tumors.

In some embodiments, the viral infection is an infection by hepatitis B virus (HBV), hepatitis C virus (HCV), human papilloma virus (HPV), human immunodeficiency virus (HIV), influenza virus, parainfluenza viruses, respiratory syncytial virus (RSV), cytomegalovirus (CMV), Epstein-Barr virus (EBV), herpes simplex viruses (HSV), papillomavirus, measles virus, or rotavirus.

In some embodiments, the bacterial infection is an infection by *Mycobacterium tuberculosis*, Helicobacters, Campylobacters, Clostridia, *Corynebacterium diphtheriae, Bordetella pertussis, Borrelia burgdorferi*, Plasmodium, *Vibrio cholera, Escherichia coli, Shigella, Salmonella typhi*, and *Neisseria gonorrhea*.

EXAMPLES

Example 1

Production of Exemplary PAAV-CD14P

A common feature of most of recombinant adeno-associated virus vectors prior to the instant disclosure was that the promoters are constitutive promoters, such as the CMV promoter, the SV40 early promoter, the AAV p5 promoter and others. The exogenous genes introduced by the previous rAAV vectors can be expressed in a variety of human cells. However, the exemplary pAAV-CD14p vectors described in the present disclosure do not have these promoters. Rather, the presently disclosed rAAV vectors have a CD14 promoter that is tissue-specific or cell-specific. The exogenous genes carried by the rAAV vectors provided herein are specifically expressed in $CD14^+$ cells, such as monocytes and DC, while having no significant and/or detectable expression in CD14-negative ($CD14^-$) cells.

FIG. 1 provides a schematic diagram of an exemplary AAV/Human CD14 promoter vector (an exemplary pAAV-CD14p). This rAAV vector is composed of human CD14 transcription promoter (614 bp), AAV type 2 inverted terminal repeat (ITR) sequences (145 base each), a multiple cloning site sequence (MCS), an SV40 late poly-A sequence (256 bp), beta lactamase gene (Ampicillin resistance gene, $Amp^r$), and a gene element that enables the plasmid to replicate in *E. coli* (such as DH5α).

The exemplary rAAV vector was prepared as follows: The pCAAV-2 plasmid containing the complete AAV-2 genome was prepared and used as a starting point. Using the AAV-2 genome sequence (GenBank: J01901.1) as a reference, the pCAAV-2 plasmid was digested with 2 restriction endonucleases (BmgB I and SnaB I) to delete all the promoters and structural genes (Rep and Cap) of AAV-2 from nt 165 to nt 4493 so that only the viral ITR sequences were retained (nt 1-164 and nt 4494-4675).

The human CD14 genome sequence (GenBank: HQ199230.1) was used as a reference to construct PCR primers targeting the CD14 promoter. The primer sequences are provided below:

Upstream primer: 5'-atgacgtggtgccaacagatgaggttc-3' (SEQ ID NO:4; nt 2986-3004; BmgB I linker);
Downstream primer: 5'-attacgtagcagatctagtctctagaggtcgataagtettccgaac-3' (SEQ ID NO:3; nt 3599-3580; MCS (SnaB I, Bgl II, Xba I) linker).

Figure 2:
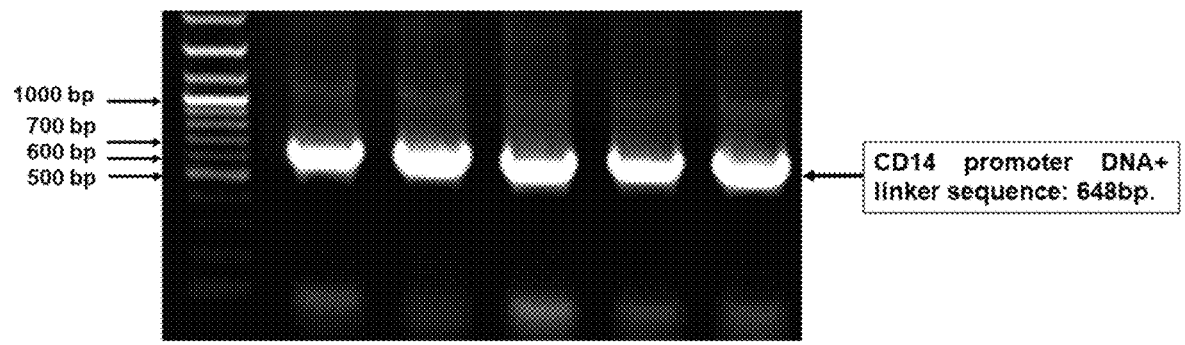
FIG. 2 illustrates gel electrophoresis results after human CD14 promoter DNA was amplified by high-fidelity PCR.
Figure 3:
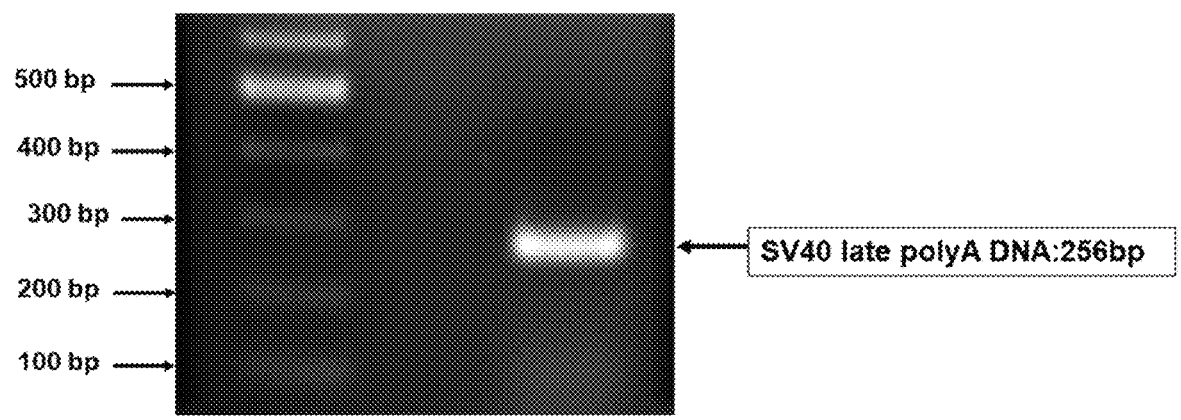
FIG. 3 illustrates gel electrophoresis result after SV40 late poly-A DNA was amplified by high-fidelity PCR.

Total DNA was isolated from human monocytes, and the CD14 promoter DNA was amplified with high-fidelity PCR (FIG. 2). The purified CD14 promoter DNA was digested with the restriction endonucleases BmgB I and SnaB I, and then ligated into the restriction endonucleases-digested pCAAV-2 plasmid. Next, the SV40 late polyA DNA sequence was inserted to the plasmid (FIG. 3) to produce the exemplary pAAV-CD14p vector.

Figure 4:
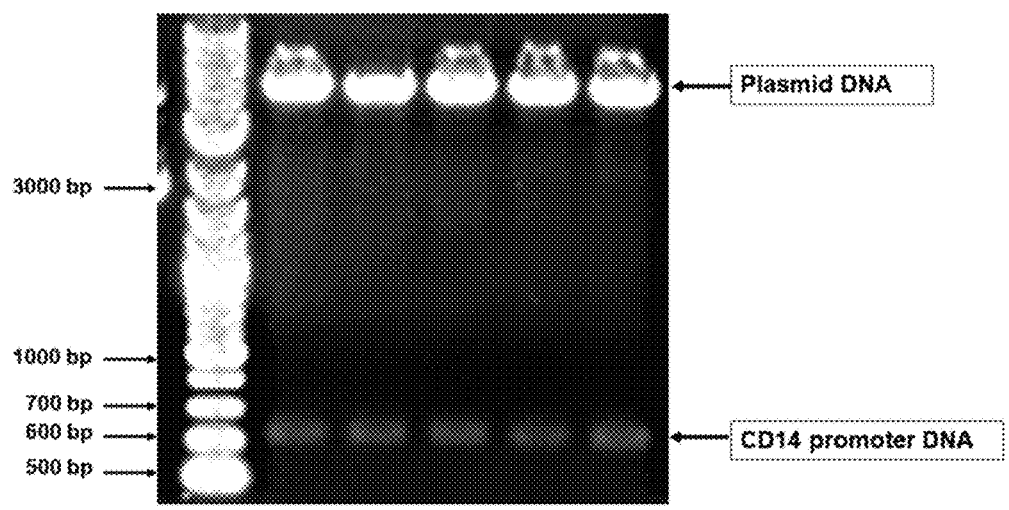
FIG. 4 illustrates gel electrophoresis results after the exemplary pAAV-CD14p plasmid was digested with the restriction endonucleases.

Insertion of the CD14 promoter into the exemplary pAAV-CD14p plasmid was confirmed by restriction enzyme digestion analysis. Specifically, the exemplary pAAV- CD14p was digested with BmgB I and SnaB I, and gel electrophoresis was performed. FIG. 4 shows bands of the correct size for the CD14 promoter DNA. In addition, the exemplary pAAV-CD14p was sequenced to confirm that the human CD14 promoter was correctly positioned, and no mutations were introduced (see the alignment between the CD14 promoter sequence in the vector and the DNA sequence in GenBank: (HQ199230.1) in FIG. 5). The exemplary pAAV-CD14p plasmid provided herein may be conveniently modified to insert an exogenous gene at the MCS (e.g., pAAV-CD14p/exogenous gene).

Example 2

Production of Infectious Virions

Figure 6:
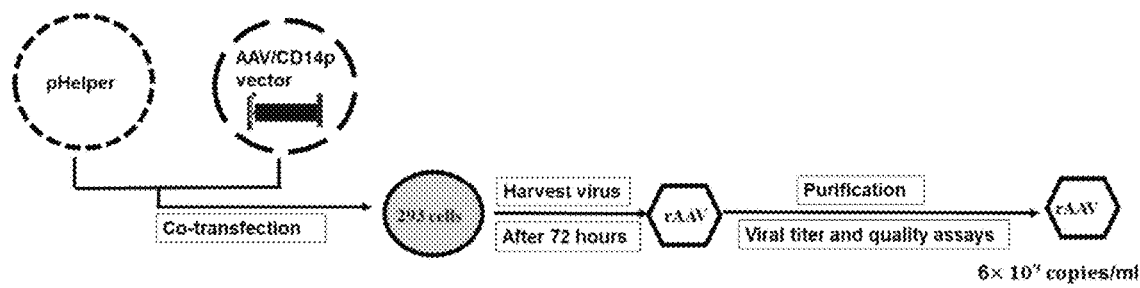
FIG. 6 illustrates the schematic diagram of an exemplary process of preparing the infectious virus particles.
Figure 7A:
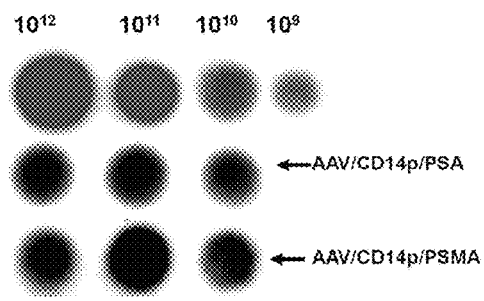
FIG. 7A illustrates rAAV viral titers (copies/ml) of rAAV-CD14p/exogenous gene virus expressing prostate specific antigen (PSA) or prostate specific membrane antigen (PSMA).
Figure 7B:
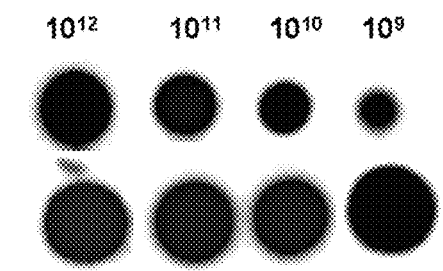
FIG. 7B illustrates rAAV viral titers of rAAV-CD14p/exogenous gene virus expressing IL-4 or IL-12.

Adeno-associated virus is a replication-defective virus, which need helper viruses (such as adenoviruses) in nature to be assembled into infectious virions. FIG. 6 illustrates a schematic diagram of preparing the infectious rAAV (rAAV-CD14p/exogenous gene) virions without a wild type helper virus and without contamination of replication-competent AAV-2. pHelper plasmid was constructed and contains the VA, E2A, E3 and E4 gene of adenovirus type 5 and Rep and Cap gene of AAV type 2, which are necessary for AAV virion assembly. A pAAV-CD14/exogenous gene plasmid was co-transfected with the pHelper plasmid into HEK 293 cells. The infectious rAAV virions were generated after 72 to 96 hours of the culture of the transfected cells. The titer of the rAAV virions was detected using a dot blot hybridization assay. A digoxigenin (DIG)-labeled DNA probe targeting the human CD14 promoter was used to detect the rAAV virion and compared to a loading standard. FIG. 7 shows high titers of infectious rAAV virions. Therefore, the instant data demonstrates that the exemplary pAAV-CD14p and pHelper plasmid systems effectively produced rAAV virions in cell culture.

Example 3

Isolation of Monocytes and Differentiation into Dendritic Cells

Peripheral venous blood was drawn from a subject. PBMCs were separated from the peripheral venous blood using Ficoll. In some experiments, monocytes were separated from the PBMCs using culture methods to separate adherent cells (monocytes) from non-adherent cells (lymphocytes). Briefly, the PBMCs were suspended in cell culture medium (AIM-V medium GIBCO) and added to a tissue-culture flask. The PBMCs were then cultured for 2-4 hours at 37° C., 5% $CO_2$ until the monocytes had adhered to the bottom of the flask. The non-adherent cells (lymphocytes) were removed and saved for additional experiments. The adherent cells (monocytes) were maintained in culture. As an alternative, in some experiments monocytes were separated from the PBMCs using sterile anti-CD14 antibody-labeled magnetic beads. This process resulted in a faction containing monocytes and a fraction containing lymphocytes from PBMCs.

Next, the monocytes were differentiated into DCs by adding cytokines, including GM-CSF, IL-4 and TNF-α, successively to induce the monocytes to differentiate into DCs. At Day 0, GM-CSF (800 IU/mL) and IL-4 (1000 IU/mL) were added to the culture medium. The medium was replaced with fresh medium and cytokines every 2 days. At day 5, TNF-α (100 IU/mL) was added to the medium. The differentiation culture resulted in mature DCs on the $6^{th}$ day of cell culture.

Example 4

CD14 Promoter Specifically Drives Exogenous Gene Expression in CD14 Expressing Cells Next, the specificity the CD14 promoter for expression of an exogenous gene was tested. First, eGFP was cloned into the exemplary pAAV-CD14p plasmid as described in Example 1 to generate pAAV-CD14p/eGFP. Next, infectious virions were generated by co-transfecting pAAV-CD14p/eGFP and pHelper into HEK 293 cells as described above, and rAAV-CD14p/eGFP virions were collected.

Figure 8A:
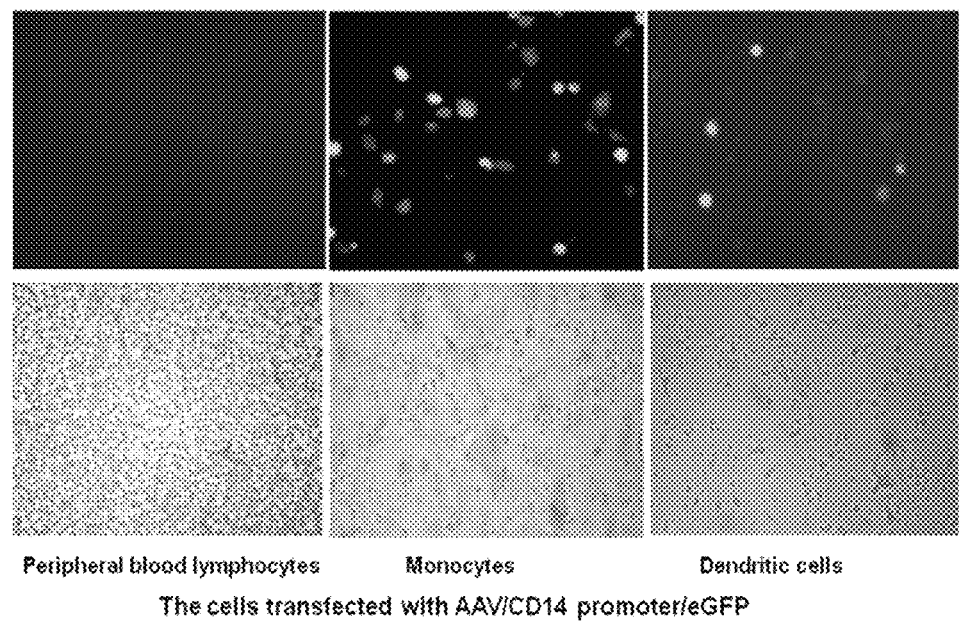
FIG. 8A illustrates CD14 promoter driven expression enhanced green fluorescent protein (eGFP) in peripheral blood lymphocytes, monocytes, and dendritic cells.
Figure 8B:
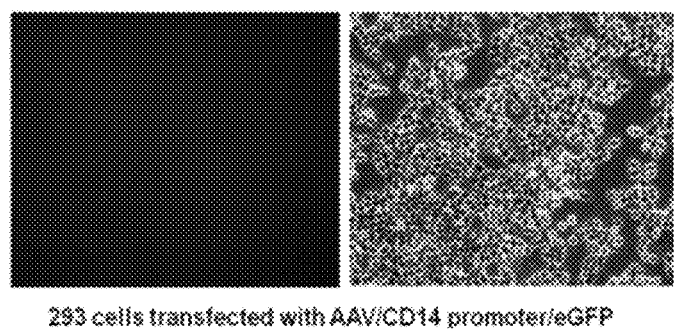
FIG. 8B illustrates lack of CD14 promoter driven eGFP expression in HEK 293 cells.

Next, $CD14^+$ monocytes and DC were transduced with AAV-CD14p/eGFP virus. CD14-peripheral blood lymphocytes and HEK 293 cells were transduced with rAAV-CD14p/eGFP virus as controls. The expression of eGFP was assessed by fluorescence microscopy. Seventy-two hours after the cells were infected by rAAV-CD14p/eGFP virus, eGFP was specifically expressed in the $CD14^+$ monocytes and dendritic cells, and not expressed in the $CD14^-$ lymphocytes and HEK 293 cells (FIG. 8). Therefore, the data demonstrate that the CD14 promoter specifically drove expression the exogenous gene products in the $CD14^+$ cells.

Example 5

Expression of Antigens in Monocytes and Dendritic Cells Transduced by RAAV-CD14P/Antigen Virions In order to test expression of cancer antigens, rAAV-CD14p/antigen virions were generated by cloning DNA sequences encoding PSA, PSMA, PAP, CEA, CK19, MAGE-A3, Survivin, or Muc-1, respectively, into the exemplary pAAV-CD14p plasmid as described in Example 1 using the methods described above. These virions are referred to as rAAV-CD14p/PSA, rAAV-CD14p/PSMA, rAAV-CD14p/PAP, rAAV-CD14p/CEA, rAAV-CD14p/CK19, rAAV-CD14p/MAGE-A3, rAAV-CD14p/Survivin, and rAAV-CD14p/Muc-1, respectively.

Monocytes were transduced with rAAV-CD14p/antigen virions and differentiated into DC in culture in order to assess CD14 promoter (CD14p) mediated expression of antigen payload in monocytes and DC. First, PBMCs were obtained from the peripheral venous blood of a human subject. Monocytes were separated from the PBMCs as described in Example 3, and cultured in cell culture medium. After the monocytes were separated, the different rAAV-CD14p/antigen viruses were immediately added to separate monocyte cultures at an MOI of 50 and cytokines were added to the culture medium as described in Example 3 to induce the monocytes to differentiate into DCs.

Figure 9:
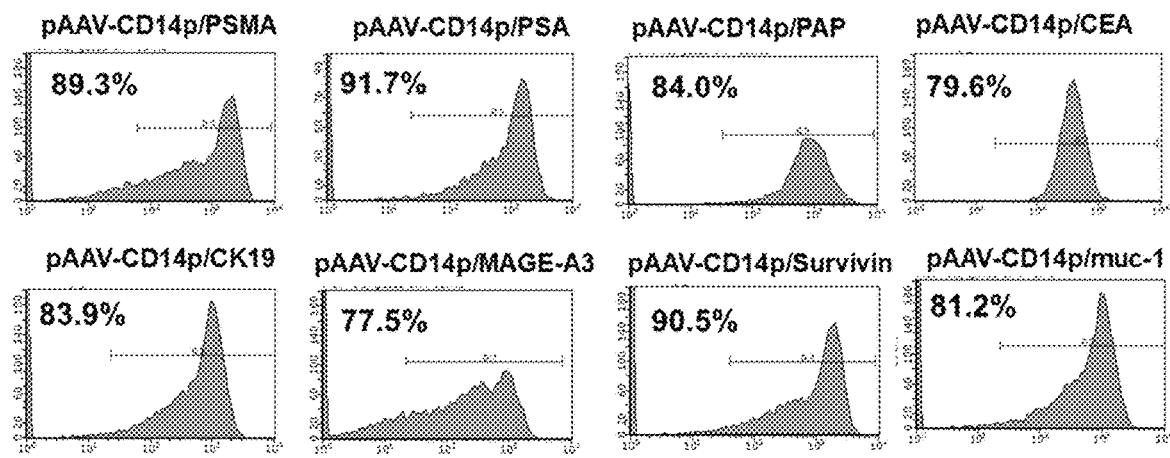
FIG. 9 shows results of flow cytometry detection of antigens expressed in monocytes and dendritic cells (DC) transduced by rAAV-CD14p/antigen rAAV on the 3rd day of the cell culture. PAP: Prostatic acid phosphatase antigen; CEA: Carcinoembryonic antigen; CK19: Cytokeratin 19 antigen; MAGE-A3: Melanoma antigen family A3 antigen; Muc-1: Mucin 1 antigen.

Expression of antigens in the monocytes and DC transduced by the different rAAV-CD14p/antigen virions was assessed on the 3rd day of post-transduction cell culture using flow cytometry. The results of the flow cytometry show that the expression rates of the antigens of the cells ranged from 79.6% to 91.7% (FIG. 9). The data indicate that the rate of antigen expression was high, and that the transduction efficiency of the rAAV-CD14p/antigen virions was also high.

Example 6

Expression of Cytokines in Dendritic Cells Transduced by RAAV-CD14P/Cytokine Virions In order to test expression of cytokines, rAAV-CD14p/cytokine virions were generated by cloning DNA sequences encoding GM-CSF or IL-4, respectively, into the exemplary pAAV-CD14p plasmid using the methods described above. These virions are referred to as rAAV-CD14p/GM-CSF and rAAV-CD14p/IL-4, respectively. Control vectors were also produced that include a constitutive p5 promoter or CMV promoter rather than the CD14 promoter, i.e., rAAV-p5/GM-CSF and rAAV-CMVp/IL-4.

Figure 10:
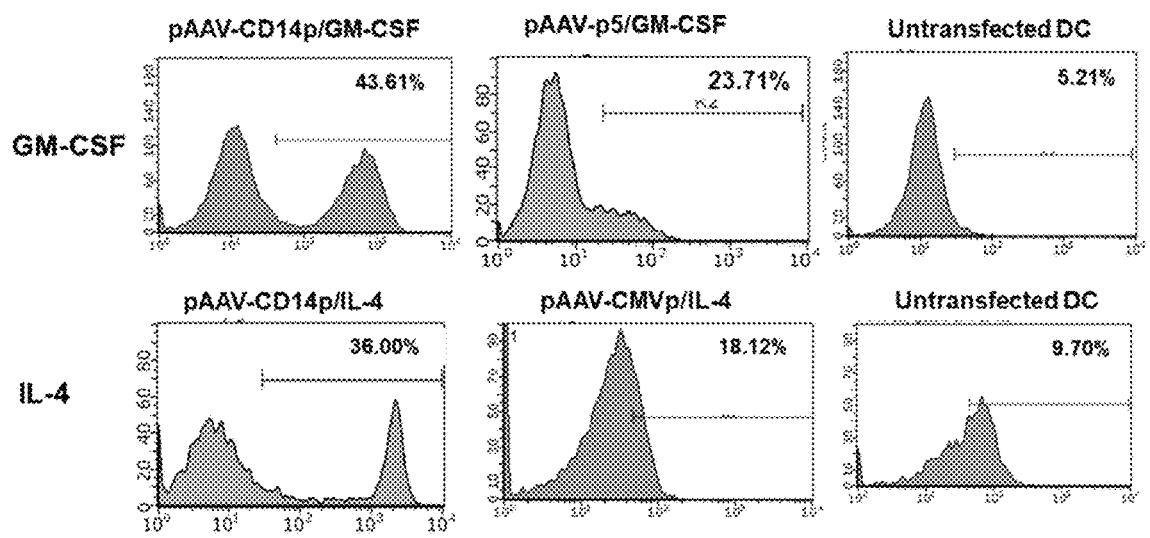
FIG. 10 shows results of flow cytometry detection cytokines in DC transduced by respective rAAV-CD14p/cytokine rAAV on the 5th day of the cell culture. GM-CSF: Granulocyte-macrophage colony-stimulating factor.

Monocytes were separated from PBMCs, transduced with rAAV-CD14p/cytokine virions, and cultured in DC differentiation culture with GM-CSF, IL-4 and TNF-α as described above. Five days after transduction, routine flow cytometry was used to detect the expression of the cytokine genes in the DCs (FIG. 10). The levels of cytokine expression in the rAAV-CD14p/cytokine virus-transduced DCs were significantly higher than those of the untransduced controls (p<0.05). The results of the flow cytometry also demonstrate the transfection efficiency of rAAV-CD14p/cytokine gene viruses was high. Surprisingly, the transduction efficiency of rAAV virions having the constitutive p5 promoter or CMV promoter was significantly lower than the rAAV-CD14p/cytokine gene viruses (p=0.02 to 0.04)

Example 7

Expression of Dendritic Cell Markers on RAAV-CD14P/Antigen-Transduced Cells The expression of markers that are important for DC activation of an antigen-specific CTLs were assessed by flow cytometry. Human CD1a, CD40, CD80 and CD86 are the markers of a DC. CD1a is a DC marker expressed early in the differentiation. CD1a$^+$ DCs produce significant quantities of IL-12 p70 upon stimulation, and generate IFN-γ-producing CD4$^+$ T cells. CD40, CD80 and CD86 molecules serve as important costimulatory molecules for DC stimulation of T cells. The increased expression of CD80, CD86 and CD40 contributes to generating a robust CTL response. CD40-CD40L is a pair of costimulatory molecules, and their interaction is important for a successful adaptive immune response, in particular the development of CD8$^+$ CTLs. CD80 is an important component in DC functions and CTL activation. When the MHC class II-peptide complex on a DC interacts with the receptor on a T helper cell, CD80 allows for interaction between the DC and CD8$^+$ T lymphocytes via CD28. The interaction via CD28 helps to signal the T lymphocytes differentiation into CTLs. CD86 provides costimulatory signals important for T lymphocyte activation and survival.

Figure 11:
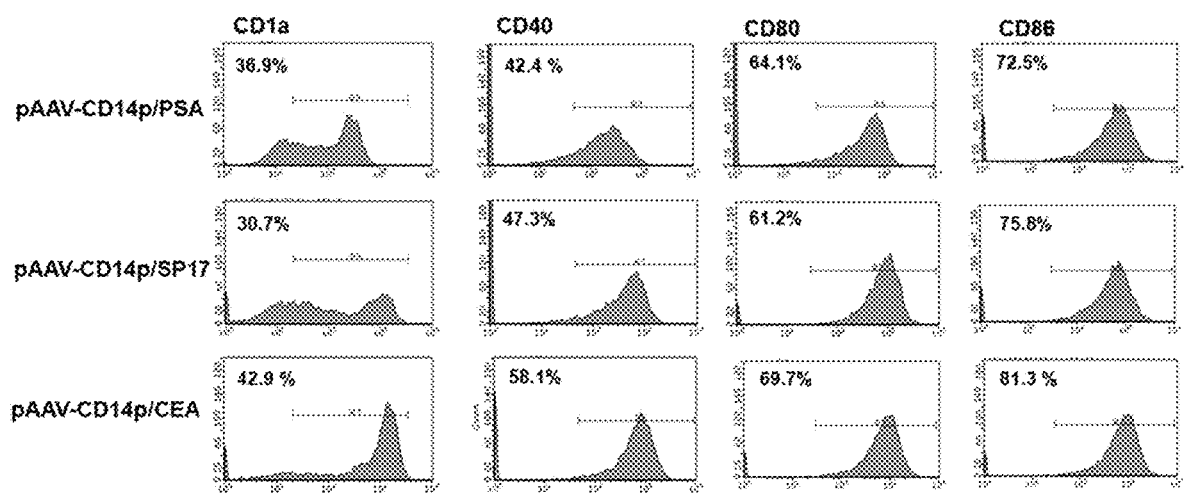
FIG. 11 shows results of flow cytometry detection of CD1a, CD40, CD80, and CD86 markers of DC cells transduced with rAAV-CD14p/antigen rAAV. SP17: Sperm protein 17.

FIG. 11 shows that CD1a, CD40, CD80 and CD86 levels of the DC transduced by the rAAV-CD14p/antigen virions were very high. The high expression levels of the rAAV-transduced DC's CD markers indicate that the DC can function to stimulate the immune response, in particular the antigen specific CTL response.

Example 8

IL-12 and IL-10 Expression in RAAV-Transduced DCs

Figure 12:
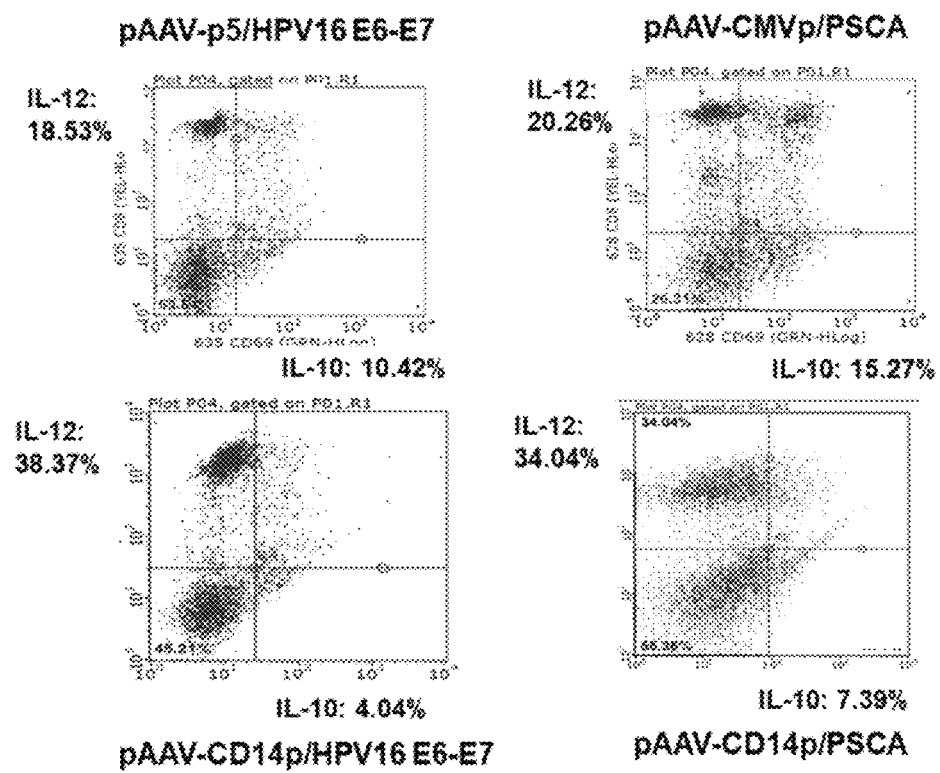
FIG. 12 shows a comparison of flow cytometry detection of IL-12 and IL-10 expression level of the rAAV-transduced DC. PSCA: Prostate stem cell antigen; HPV16 E6-E7: Human papillomavirus type 16 E6 and E7 antigen.

Expression of IL-12 and IL-10 was measured in DCs transduced with rAAV-CD14p/antigen virions. IL-12 and IL-10 are thought to play contrasting roles in the DC mediated immune response. High expression of IL-12 in DC is thought to enhance the Th1 response and increase CTL proliferation. In contrast, expression of IL-10 is thought to enhance the Th2 response. DCs transduced with rAAV-CD14p/HPV16 E6-E7 or rAAV-CD14p/PSCA virions were compared to DCs transduced with virions having an AAV type p5 promoter or CMV promoter, i.e., rAAV-p5/HPV16 E6-E7 or rAAV-CMVp/PSCA. The p5 promoter or CMV promoter can express exogenous genes in various human cells, including CD14-negative cells. Monocytes were separated from PBMCs, transduced with rAAV virions, and differentiated to DCs as described above. As shown in FIG. 12, the levels of IL-12 expressed by the rAAV-CD14p/antigen virion transduced DCs were significantly higher than those of the controls (p<0.05).

The data indicate that the expression level of IL-12 were upregulated, and the expression level of IL-10 were downregulated after the monocytes and DCs were transfected by the rAAV-CD14p/antigen gene viruses. The rAAV-CD14p/antigen virion-transduced DCs were more efficient in enhancing the killing ability of the antigen-specific CTLs than the DCs transfected by the rAAV with AAV type p5 promoter or CMV promoter.

Example 9

Efficiency of Differentiation of Monocytes into DCs

Figure 13:
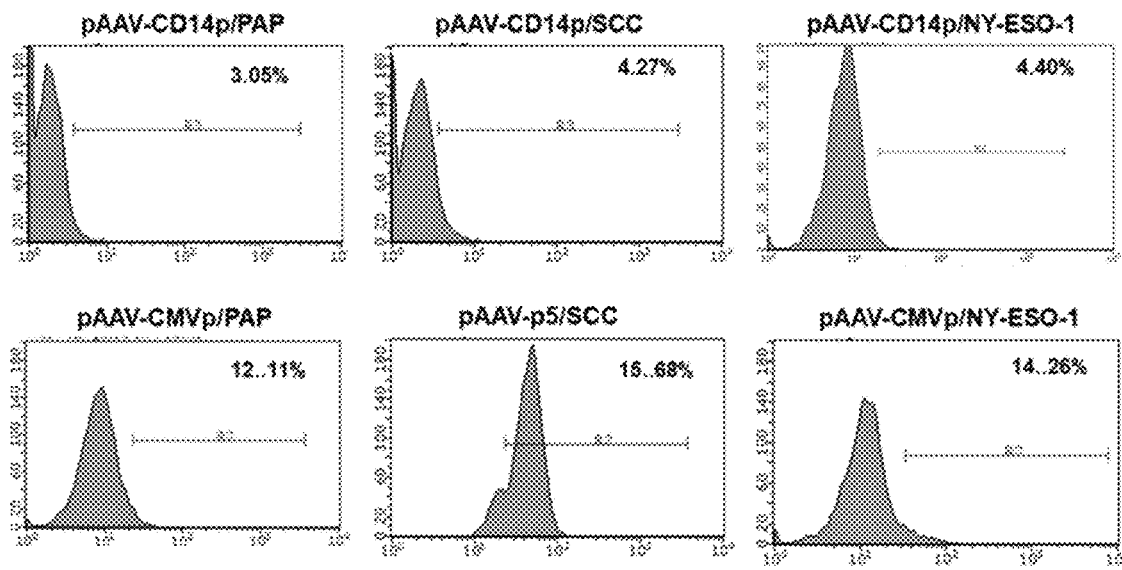
FIG. 13 shows results of flow cytometry detection of the number of the monocytes remaining on the 6th day of DC culture. SCC: Squamous cell carcinoma antigen; NY-ESO-1: New York Esophageal Squamous Cell Carcinoma-1 antigen.

Human CD14$^+$ monocytes were cultured in the presence of GM-CSF, IL-4 and TNF-α as described above to differentiate the cells into DCs. On the 6th day of the cell culture, a large number of DCs were detected. In order to assess differentiation efficiency, the number of remaining monocytes in culture were detected by flow cytometry. The results showed that the numbers of the remaining monocytes transduced by the rAAV-CD14p/antigen virion were significantly lower than those of the remaining monocytes transduced by the rAAV-p5/antigen virion or rAAV-CMVp/antigen virion (p<0.05) (FIG. 13). These results unexpectedly show that by transducing human CD14$^+$ monocytes with the rAAV-CD14p/antigen virion, more DCs can be obtained.

Example 10

DC Induction of IFN-γ Expression in Lymphocytes

The ability of rAAV transduced DCs to activate Th1 response was assessed by co-culturing DC cells with lymphocytes and measuring IFN-γ expression. IFN-γ is an important Th1 cytokine. Expression of IFN-γ by T lymphocytes is positively correlated with the ability of the antigen-specific CTLs to kill the antigen-positive target cells.

Monocytes were transduced with rAAV-CD14p/antigen virions or rAAV-CMVp/antigen virions and cultured in differentiation culture as described above for 6 days. The monocytes were transduced with rAAV-CD14p/HPV18 E6-E7, rAAV-CD14p/CEA, rAAV-CD14p/MAGE-C2, rAAV-CMVp/HPV18 E6-E7, rAAV-CMVp/CEA, or rAAV-CMVp/MAGE-C2. On the 6th day of the cell culture, DCs were harvested and mixed with the lymphocytes that were harvested from the same donor as the monocytes. The DCs and lymphocytes were co-cultured in the presence of IL-7 (80 IU/mL) and IL-2 (100 IU/mL). The medium and cytokines were replaced every two days. On the 14$^{th}$ day of cell culture, lymphocytes were harvested, and expression levels of IFN-γ were measured by flow cytometry.

Figure 14:
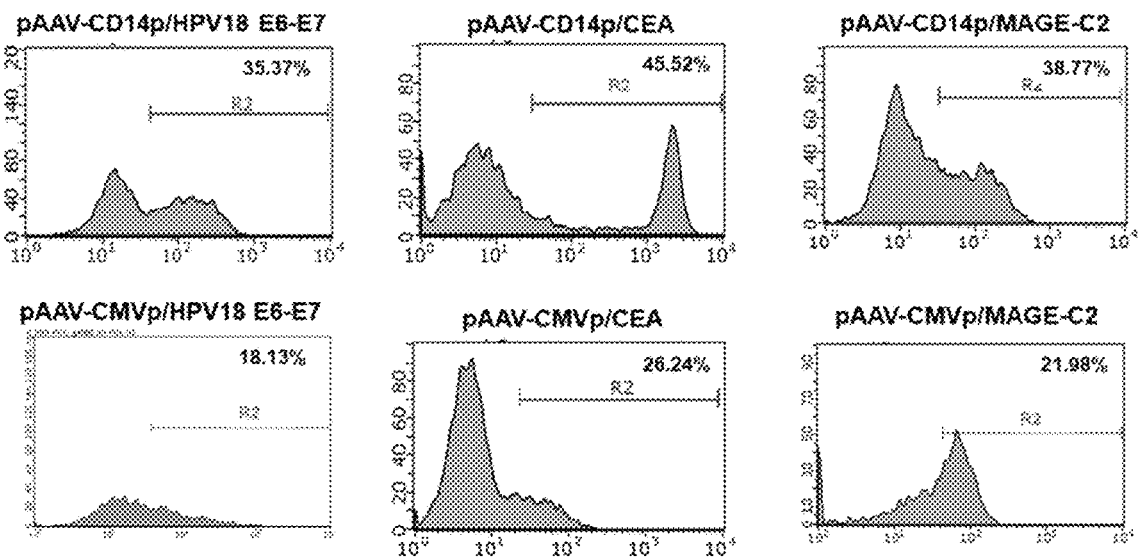
FIG. 14 illustrates IFN-γ expression level of the T lymphocytes primed by rAAV-CD14p/antigen rAAV-transduced DC compared to rAAV-CMVp/antigen rAAV-transduced DC, respectively. HPV18 E6-E7: Human papillomavirus type 18 E6 and E7 antigen; MAGE-C2: Melanoma antigen family C2 antigen.

The results show that the IFN-γ levels expressed by the T lymphocytes activated by the rAAV-CD14p/antigen gene virus-transfected DC were significantly higher than the IFN-γ levels expressed by the T lymphocytes activated by the rAAV-CMVp/antigen gene virus-transfected DC (FIG. 14; p<0.05). This may be due to the higher number of rAAV-CD14p/antigen transduced DCs compared to the number of rAAV-CMVp/antigen DC, resulting in an increased generation of CTLs. In other words, the rAAV having a CD14 promoter are surprisingly more efficient at inducing lymphocytes to express IFN-γ.

Example 11

Lymphocyte Expression of CD69 and CD8

The expression levels of CD69 and CD8 were assessed in T lymphocytes co-cultured with rAAV-CD14/antigen virion transduced DCs. CD69 is a marker of early activation of CTL (CD8$^+$ T lymphocytes). Monocytes were transduced with rAAV-CD14p/antigen virions, rAAV-CMVp/antigen virions, or rAAV-p5/antigen virions, and cultured in differentiation culture as described above for 6 days. More specifically, the monocytes were transduced with rAAV-CD14p/HPV16 E6-E7, rAAV-CD14p/CK19, rAAV-CD14p/BA46, rAAV-CMVp/HPV16 E6-E7, rAAV-p5/CL19, or rAAV-CMVp/BA46. On the 6th day of the cell culture, DC were harvested and mixed with the lymphocytes harvested from the same donor as the monocytes. The DCs and lymphocytes were co-cultured in the presence of IL-7 and IL-2 as described above. On the 14th day of DC and T lymphocyte co-culture, flow cytometry was used to detect the number of the CD69$^+$/CD8$^+$ T lymphocytes in T cell population.

Figure 15:
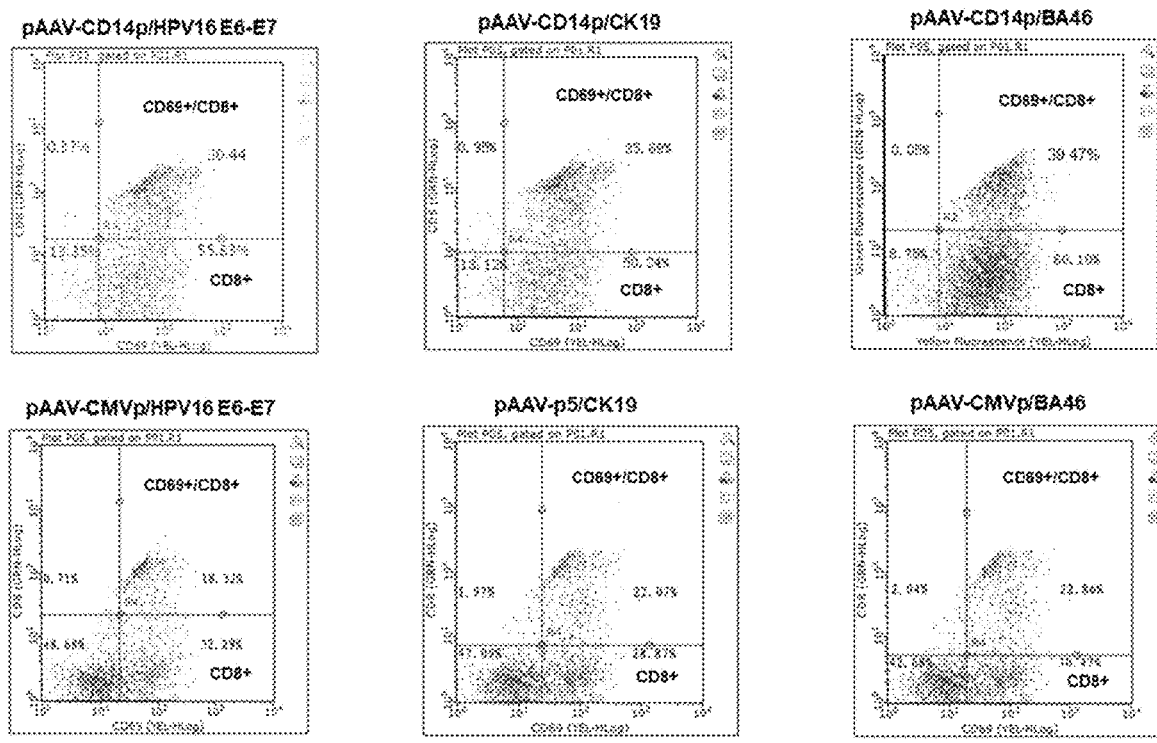
FIG. 15 illustrates the number of the CD69+/CD8+ T lymphocytes primed by rAAV-CD14p/antigen rAAV-transduced DC, rAAV-p5/antigen rAAV-transduced DC or rAAV-CMVp/antigen rAAV-transduced DC, respectively. BA46: Breast epithelial antigen 46 (lactadherin).

The results showed that the number of the CD69$^+$/CD8$^+$ T lymphocytes activated by the rAAV-CD14p/antigen gene virus-transfected DC were much more than that of the CD69$^+$/CD8$^+$ T lymphocytes activated by the rAAV-p5/antigen gene virus or rAAV-CMVp/antigen gene virus-transfected DCs (FIG. 15). The data indicates that the rAAV-CD14p/antigen virions are more efficient than p5 or CMV driven virions in generating T lymphocytes with robust killing activities toward target cells.

Example 12

Cytotoxic T Lymphocyte Killing of Target Cells

Monocytes were transduced by rAAV virions and differentiated to DC as described above. The DCs were co-cultured with donor lymphocytes as described above. The monocytes were transduced with rAAV-CD14p/HPV16 E6-E7, rAAV-CD14p/PSMA, or rAAV-CD14p/MAGE-A3. On the 14th day of DCs and T lymphocytes co-culture, the cells were harvested. CTLs were co-cultured with cells that were isolated from tumor tissues expressing the respective viral or tumor antigens, i.e., HPV-16 E6 and E7 antigen positive cervical cancer cells, PSMA positive prostate cancer cells, and MAGE-A3 positive non-small cell lung adenocarcinoma cells. A routine chromium ($^{51}$Cr) release assay was used to analyze the killing activity of the CTLs primed by the rAAV-CD14p/antigen transduced DCs.

Figure 16:
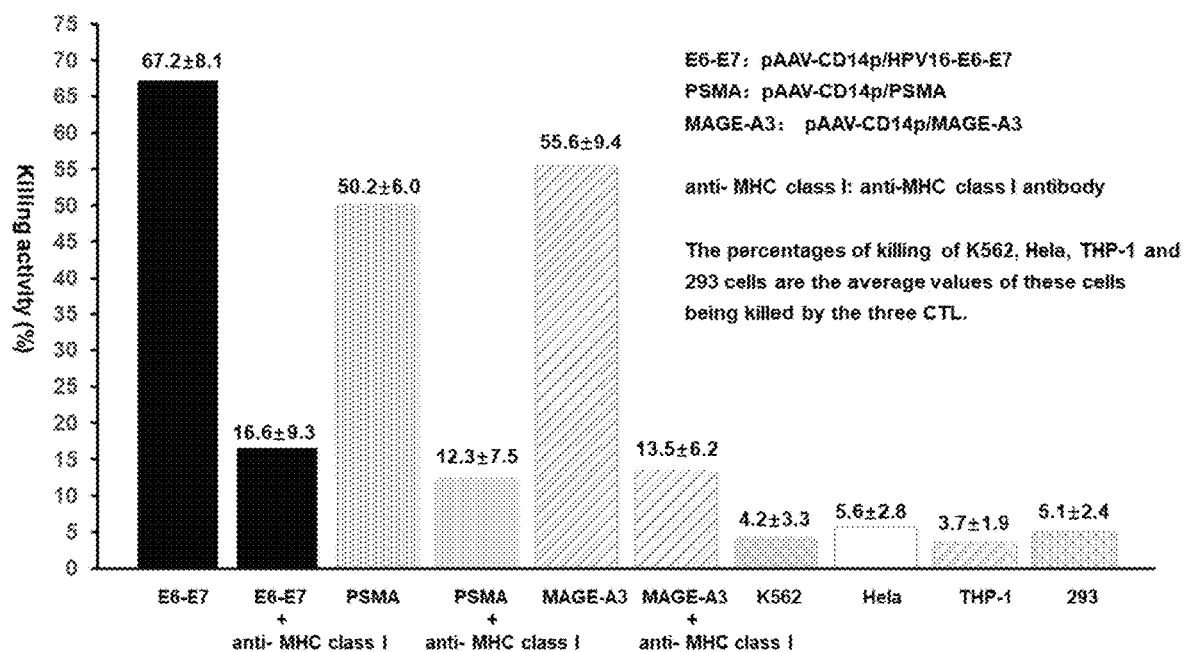
FIG. 16 illustrates the killing activity of the cytotoxic T lymphocytes (CTL) elicited by rAAV-CD14p/antigen rAAV-transduced DC or rAAV-transduced DC treated with anti-MHC class I antibodies. The percentage of killing of K562, Hela, THP-1, or HEK 293 cells is the average value of these cells killed by the CTLs exposed to three different rAAV-CD14p/antigen rAAV-transduced DC.

FIG. 16 shows that the percentages of one-time killing of the tumor antigen-positive and viral antigen-positive target cells of the CTLs primed by the rAAV-CD14p/antigen transduced DCs were about 50.2% to 67.2%. In control experiments, anti-human MHC class I antibodies were added to the cell culture 6 hours before co-culture with CTLs, and the percentages of one-time killing of the tumor antigen-positive and viral antigen-positive target cells were about 12.3 to 16.6. Therefore, the anti-MHC-I antibodies drastically reduced the killing of the antigen-positive cells (FIG. 16). In addition, a series of the antigen-negative control cells were not killed (FIG. 16). The results demonstrate that the rAAV-CD14p/antigen transduced DC cell were able to activate antigen specific CTL killing of target cells in a MHC-I-restricted manner.

Figure 17:
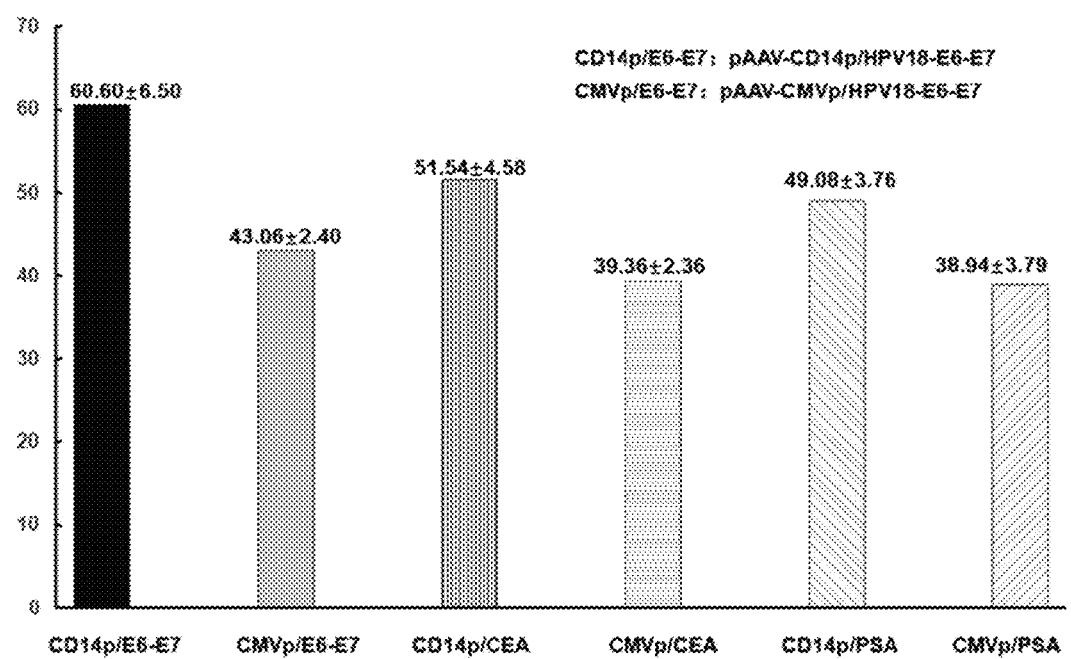
FIG. 17 shows a comparison of the killing activity of the CTLs elicited by rAAV-CD14p/antigen rAAV-transduced DC and rAAV-CMVp/antigen rAAV-transduced DC.

Next, the CTL killing activated by the DC transduced with rAAV-CD14p/HPV18 E6-E7, rAAV-CD14p/CEA, rAAV-CD14p/PSA, rAAV-CMVp/HPV18 E6-E7, rAAV-CMVp/CEA, or rAAV-CMVp/PSA were compared. The modified DC were generated and co-cultured with donor lymphocytes as described above. CTLs were co-cultured with cells that were isolated from tumor tissues expressing the respective viral or tumor antigens, i.e., HPV-18 E6 and E7 antigen positive cervical cancer cells, PSA positive prostate cancer cells, and CEA positive non-small cell lung adenocarcinoma cells. Killing activity was assessed by co-culture of CTL with antigen expressing target cells and $^{51}$Cr release assay. The percentages of the target cells killed by the CTL elicited by the rAAV-CD14p/antigen-transduced DC were significantly higher than that of the target cells killed by the CTL elicited by the rAAV-CMVp/antigen-transduced DC (p<0.05) (FIG. 17). The results surprisingly demonstrate a more robust antigen specific killing activity of the CTLs activated by the rAAV-CD14p/antigen transduced DCs than the CTLs activated by the rAAV-CMVp/antigen transduced DCs.

Example 13

Cytotoxic T Lymphocyte Killing of Target Cells

Experiments were performed to assess the rAAV-CD14p/antigen specificity in a mixed culture of PBMC. Human PBMC are mainly composed of lymphocytes and a small number of monocytes. CD3 is the marker of T lymphocytes. In this study, human PBMC were directly infected with the rAAV. The rAAV was rAAV-CD14p/antigen virus, rAAV-CMVp/antigen virus, or rAAV-p5/antigen virus. More specifically, rAAV-CD14p/CK19, rAAV-CD14p/muc-1, rAAV-p5/CK19, or rAAV-p5/muc-1. GM-CSF, IL-4 and TNF-α were added into the PBMC culture to promote differentiation of monocytes into DC. On day 6 of culture, IL-2 and IL7 were added as described above. The cell culture medium and cytokines were replaced every two days. On day 14, the PBMC were harvest and the number of CD3$^+$ T lymphocytes was analyzed by flow cytometry.

Figure 18:
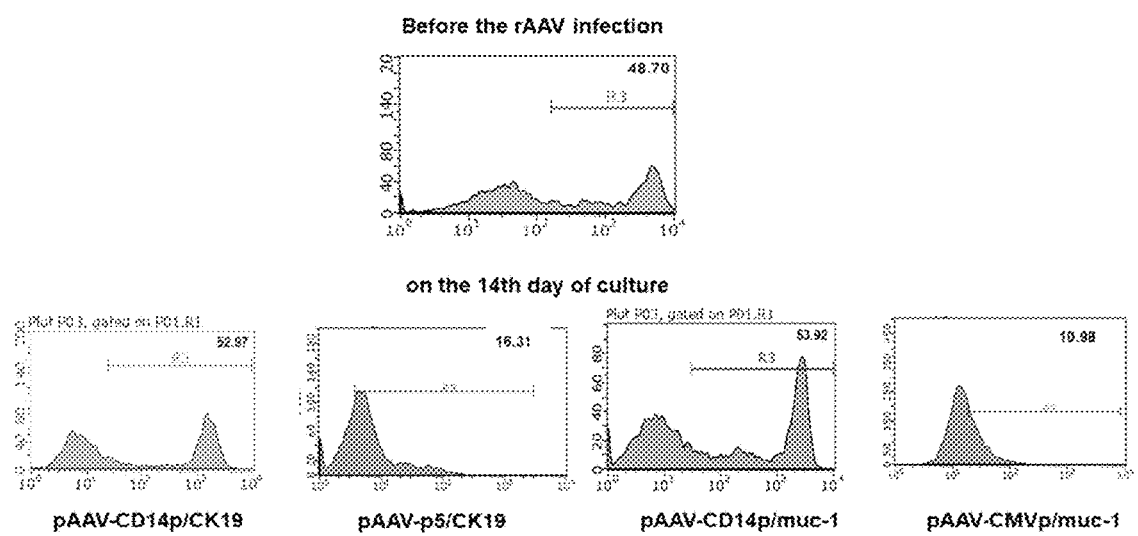
FIG. 18 illustrates the percentage of the CD3+ T lymphocytes in the peripheral blood mononuclear cells (PBMC) before the rAAV transduction and on the 14$^{th}$ day after transduction with rAAV-CD14p/CK19, rAAV-p5/CK19, rAAV-CD14p/muc-1, rAAV-CMVp/muc-1, respectively.

The results (FIG. 18) demonstrate that the number of CD3$^+$ T lymphocytes in the rAAV-CD14p/antigen-transduced PBMC increased by day 14 compared to the number of CD3$^+$ cells before transduction at day 0. In contrast, the number of CD3$^+$ cells in the rAAV-p5/antigen- and rAAV-CMVp/antigen-transduced PBMC were significantly reduced. The reduced number of CD3$^+$ cells in the rAAV-p5/antigen or rAAV-CMVp/antigen-transduced PBMC is thought to be the result of on-target, off-tissue killing by activated CTL. The p5 promoter and CMV promoter are constitutive promoters, so the CD3$^+$ cells transduced by rAAV-p5/antigen or rAAV-CMVp/antigen virions also express the antigen, and are targeted by antigen specific CTL. In contrast, the CD14 promoter specifically drives expression of the antigen in the DCs. Therefore, while the rAAV-CD14p/antigen virions can infect the CD3+ T lymphocytes, the CD3+ cells do not express the antigen and are not killed by antigen specific CTL in culture.

Accordingly, this study not only suggests that the application of rAAV-CD14p/antigen virions in cellular immunotherapy is safer, but also provides a new and rapid method for preparing CTLs. According to the results of the study, the PBMCs may be directly infected by rAAV-CD14p/antigen gene virus to prepare the CTLs without first separating monocytes from the PBMC. In contrast, previous methods of preparing CTL activated by DC required the first step of separating monocytes from PBMC.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A polynucleotide comprising a recombinant adeno-associated virus (rAAV) vector encoding two inverted terminal repeat (ITR) sequences further comprising a CD14 promoter operably linked to an exogenous nucleic acid sequence, wherein the CD14 promoter drives expression of the exogenous nucleic acid specifically in a CD14-expressing cell, and wherein the exogenous nucleic acid sequence comprises a sequence encoding a tumor antigen, a tumor-associated antigen, or an oncogene product.

2. The polynucleotide of claim 1, wherein the CD14 promoter is a human CD14 promoter sequence.

3. The polynucleotide of claim 1, wherein the CD14 promoter comprises SEQ ID NO:1.

4. The polynucleotide of any one of claim 1, wherein the CD14 promoter comprises at least the nucleotides at positions 378-386, positions 404-410, and positions 533-538 of SEQ ID NO:1.

5. The polynucleotide of claim 1, wherein the rAAV vector comprises in the 5' to 3' direction a first ITR, the CD14 promoter operably linked to the exogenous nucleic acid sequence, a polyadenylation signal sequence, and a second ITR.

6. The polynucleotide of claim 5, wherein the first ITR sequence and the second ITR sequence are an AAV-2 ITR.

7. The polynucleotide of claim 1, wherein the rAAV vector is a plasmid.

8. The polynucleotide of claim 7, wherein the plasmid comprises the CD14 promoter operably linked to the exogenous nucleic acid sequence, AAV type 2 ITR sequences, an SV40 late poly-A sequence, an antibiotic resistance gene, and a gene element that enables the plasmid to replicate in a host cell, wherein the CD14 promoter is a human CD14 promoter.

9. The polynucleotide of claim 1, wherein the tumor antigen, the tumor-associated antigen, or the oncogene product is an alpha fetoprotein (AFP), B melanoma antigen (BAGE/CT2.1), Cluster of Differentiation 20 (CD20), CD269, G250 (carbonic anhydrase IX/CA IX), HM1.24, CD154, a prostate cancer-associated antigen, a breast cancer-related tumor associated antigen, a member of the cancer-testis antigen (CT) family, a member of the human melanoma-associated antigen (MAGE) family, MART 1, SAGE 1, carcinoembryonic antigen (CEA), HER-2/neu, cytokeratin 19 (CK19, K19, cyfra21-1), Survivin, Mucin-1 (MUC-1, CA15-3), Squamous cell carcinoma (SCC) antigen, or any antigenic fragment and/or combination thereof.

10. The polynucleotide of claim 9, wherein:
(a) the prostate cancer-associated antigen is prostate specific antigen (PSA), prostate specific membrane antigen (PSMA), prostate stem cell antigen (PSCA) or prostatic acid phosphatase (PAP) antigen, or any antigenic fragment and/or combination thereof;
(b) the breast cancer-related tumor associated antigen is breast epithelial antigen 46 (BA46, lactadherin) or any antigenic fragment thereof,
(c) the member of the CT family is New York Esophageal Squamous Cell Carcinoma-1 (NY-ESO-1) (CT6.1), ADAM2 (CT15), SPA17 (CT22), or SPANX-A1 (CT11.1), or any antigenic fragment and/or combination thereof; or
(d) the member of the MAGE family is MAGE-A1/CT1.1, MAGE-A2/CT1.2, MAGE-A3/CT1.3, MAGE-A4/CT1.4, MAGE-B1/CT3.1, MAGE-C1/CT7.1, MAGE-C2/CT10, MAGE-C3/CT7.2, or MAGE-E1, or any antigenic fragment and/or combination thereof.

11. The polynucleotide of claim 9, wherein the tumor antigen, the tumor-associated antigen, or the oncogene product is PSA, PSMA, PAP, PSCA, BA46, CEA, HER-2/neu, CK19, Survivin, MUC-1, SCC, MAGE-A1, MAGE-A2, MAGE-A3, MAGE-A4, MAGE-C2, NY-ESO-1, ADAM2, SPA17, or SPANX-A1 or any antigenic fragment and/or combination thereof.

12. A cell comprising the polynucleotide of claim 1, wherein the cell is a dendritic cell.

13. A rAAV virion comprising a polynucleotide encoding a CD14 promoter operably linked to an exogenous nucleic acid sequence, wherein the CD14 promoter drives expression of the exogenous nucleic acid specifically in a CD14-expressing cell, and wherein the exogenous nucleic acid sequence comprises a sequence encoding a tumor antigen, a tumor-associated antigen, or an oncogene product.

14. The rAAV virion of claim 13, wherein the virion comprises capsid proteins of AAV1, AAV2, AAV3, AAV4, AAV5, AAV6, AAV7, AAV8, AAV9, AAV10, AAV11, or any combination thereof.

15. The rAAV virion of claim 13, wherein the virion comprises capsid proteins of AAV2.

16. The rAAV virion of claim 13, wherein the tumor antigen, the tumor-associated antigen, or the oncogene product is AFP, a BAGE (CT2.1), CD20, CD269, G250 (CA-IX), HM1.24, CD145, a prostate cancer-associated antigen, a breast cancer-related tumor associated antigen, a member of the CT family, a member of the MAGE family, MART 1, SAGE 1, CEA, HER-2/neu, CK19 (K19, cyfra21-1), Survivin, MUC-1 (CA15-3), SCC antigen, or any antigenic fragment and/or combination thereof.

17. The rAAV virion of claim 16, wherein
   (a) the prostate cancer-associated antigen is PSA, PSMA, PSCA or PAP antigen, or any antigenic fragment and/or combination thereof;
   (b) the breast cancer-related tumor associated antigen is BA46 (lactadherin) or any antigenic fragment thereof,
   (c) the member of the CT family is NY-ESO-1 (CT6.1), ADAM2 (CT15), SPA17 (CT22), or SPANX-A1 (CT11.1), or any antigenic fragment and/or combination thereof; or
   (d) the member of the MAGE family is MAGE-A1/CT1.1, MAGE-A2/CT1.2, MAGE-A3/CT1.3, MAGE-A4/CT1.4, MAGE-B1/CT3.1, MAGE-C1/CT7.1, MAGE-C2/CT10, MAGE-C3/CT7.2, or MAGE-E1, or any antigenic fragment and/or combination thereof.

18. The rAAV virion of claim 13, wherein the tumor antigen, the tumor-associated antigen, or the oncogene product is PSA, PSMA, PAP, PSCA, BA46, CEA, HER-2/neu, CK19, Survivin, MUC-1, SCC, MAGE-A1, MAGE-A2, MAGE-A3, MAGE-A4, MAGE-C2, NY-ESO-1, ADAM2, SPA17, or SPANX-A1 or any antigenic fragment and/or combination thereof.

19. A polynucleotide comprising a rAAV vector encoding two ITR sequences and a CD14 promoter operably linked to an exogenous nucleic acid sequence, wherein the CD14 promoter drives expression of the exogenous nucleic acid specifically in a CD14-expressing cell, and the exogenous nucleic acid sequence comprises a sequence encoding:
   (a) a viral antigen selected from a group consisting of a hepatitis C virus (HCV) antigen, human papilloma virus (HPV) antigen, human immunodeficiency virus (HIV) antigen; or
   (b) a cytokine selected from the group consisting of TNF-α, TNF-β, IL-2, IL-4, IL-5, IL-7, IL-9, IFNγ, IL-13, IL-15, IL-18, IL-25, IL-27, and amphiregulin.

20. The polynucleotide of claim 19, wherein the HPV antigen is an E6 antigen or an E7 antigen.

21. The polynucleotide of claim 20, wherein the E6 antigen or the E7 antigen is from at least one HPV serotype selected from the serotypes 16, 18, 30, 31, 33, 35, 39, 45, 51, 52, 56, 58, and 61.

22. A method of treating a melanoma or a head and neck squamous cell carcinoma (HNSCC) in a subject, the method comprising:
   a. infecting peripheral blood mononuclear cells (PBMCs) of the subject with an rAAV virion comprising a polynucleotide encoding a CD14 promoter operably linked to an exogenous nucleic acid sequence, wherein the CD14 promoter drives expression of the exogenous nucleic acid specifically in a CD14-expressing cell to generate infected PBMCs, wherein the infected PBMCs comprise one or more monocytes and one or more cytotoxic T lymphocytes (CTLs), and wherein the exogenous nucleic acid sequence is exogenous to the rAAV,
   b. adding a differentiating cytokine to differentiate one or more of the monocytes of the infected PBMCs into dendritic cells (DCs),
   c. adding an activating cytokine to activate one or more cytotoxic T lymphocytes (CTLs) of the CTLs infected PBMCs to generate activated CTLs,
   d. optionally isolating the activated CTLs from the infected PBMCs, and
   e. administering an effective amount of the infected PMBCs that comprise the activated CTLs or the isolated activated CTLs to the subject.

23. The method of claim 22, wherein the differentiating cytokine is GM-CSF, IL-4, TNF-α, or any combination thereof.

24. The method of claim 22, wherein the activating cytokine is IL-2, IL-7, or both.

25. The method of claim 22, wherein the exogenous nucleic acid sequence encodes at least one antigen from the melanoma or the HNSCC, wherein the antigen comprises all or part of a tumor antigen, a tumor-associated antigen, an oncogene product, a viral antigen, or any combination thereof.

26. The method of claim 25, wherein the exogenous nucleic acid sequence comprises a sequence encoding a tumor antigen, a tumor-associated antigen, or an oncogene product, wherein the tumor antigen, the tumor-associated antigen, or the oncogene product is a BAGE (CT2.1), G250 (CA-IX), a member of the MAGE family, MART 1, SAGE 1, CEA, HER-2/neu, CK19 (K19, cyfra21-1), Survivin, MUC-1 (CA15-3), SCC antigen, or any antigenic fragment and/or combination thereof.

27. The method of claim 26, wherein the member of the MAGE family is MAGE-A1/CT1.1, MAGE-A2/CT1.2, MAGE-A3/CT1.3, MAGE-A4/CT1.4, MAGE-B1/CT3.1, MAGE-C1/CT7.1, MAGE-C2/CT10, MAGE-C3/CT7.2, or MAGE-E1, or any antigenic fragment and/or combination thereof.

28. The method of claim 26, wherein the tumor antigen, the tumor-associated antigen, or the oncogene product is CEA, HER-2/neu, CK19, Survivin, MUC-1, SCC, MAGE-A1, MAGE-A2, MAGE-A3, MAGE-A4, MAGE-C2, SPA17, or any antigenic fragment and/or combination thereof.

29. The method of claim 25, wherein the exogenous nucleic acid sequence comprises a sequence encoding a viral antigen, wherein the viral antigen is an HPV E6 antigen or an HPV E7 antigen or any antigenic fragment and/or combination thereof.

30. The method of claim 29, wherein the E6 antigen or the E7 antigen is from at least one HPV serotype selected from the serotypes 16, 18, 30, 31, 33, 35, 39, 45, 51, 52, 56, 58, and 61.

\* \* \* \* \*

UNITED STATES PATENT AND TRADEMARK OFFICE
CERTIFICATE OF CORRECTION

| | | |
|---|---|---|
| PATENT NO. | : 11,761,020 B2 | Page 1 of 1 |
| APPLICATION NO. | : 17/501973 | |
| DATED | : September 19, 2023 | |
| INVENTOR(S) | : Aiquan Chang et al. | |

It is certified that error appears in the above-identified patent and that said Letters Patent is hereby corrected as shown below:

In the Claims

Column 35, Claim 4, Line 34:
"polynucleotide of any one of claim 1, wherein"
Should read:
--polynucleotide of claim 1, wherein--.

Column 37, Claim 17, Line 5:
"or PAP antigen, or any"
Should read:
--or PAP, or any--.

Column 37, Claim 22, Line 51:
"acid sequence, wherein the CD14"
Should read:
--acid sequence, encoding at least one antigen from the melanoma or the HNSCC, wherein the DC14--.

Column 38, Claim 22, Line 13:
"PMBCs"
Should read:
--PBMCs--.

Signed and Sealed this
Thirty-first Day of December, 2024

Derrick Brent
*Acting Director of the United States Patent and Trademark Office*